United States Patent
Ngo-Chu et al.

(10) Patent No.: US 10,888,382 B2
(45) Date of Patent: Jan. 12, 2021

(54) MOUNTED PATIENT TRACKING COMPONENT FOR SURGICAL NAVIGATION SYSTEM

(71) Applicant: Acclarent, Inc., Irvine, CA (US)

(72) Inventors: Don Q. Ngo-Chu, Irvine, CA (US); Nawid E. Mehrzai, Mission Viejo, CA (US); Azhang Hamlekhan, Irvine, CA (US); Jetmir Palushi, Irvine, CA (US); Fatemeh Akbarian, Rancho Palos Verdes, CA (US); Ian Farrington, Los Angeles, CA (US); Anthanasios Papadakis, Newport Beach, CA (US)

(73) Assignee: Acclarent, Inc., Irvine, CA (US)

( * ) Notice: Subject to any disclaimer, the term of this patent is extended or adjusted under 35 U.S.C. 154(b) by 342 days.

(21) Appl. No.: 15/841,538

(22) Filed: Dec. 14, 2017

(65) Prior Publication Data

US 2019/0183582 A1 Jun. 20, 2019

(51) Int. Cl.
*A61B 34/20* (2016.01)
*A61B 5/00* (2006.01)
(Continued)

(52) U.S. Cl.
CPC .............. *A61B 34/20* (2016.02); *A61B 1/233* (2013.01); *A61B 5/062* (2013.01); *A61B 5/6814* (2013.01);
(Continued)

(58) Field of Classification Search
CPC ..... A61B 34/20; A61B 5/6814; A61B 5/6852; A61B 5/6851; A61B 17/24; A61B 5/6833;
(Continued)

(56) References Cited

U.S. PATENT DOCUMENTS 5,935,061 A * 8/1999 Acker .................. A61B 5/1076
600/304
6,618,612 B1 9/2003 Acker et al.
(Continued)

FOREIGN PATENT DOCUMENTS

DE 102013210969 A1 12/2014
EP 3028631 A1 6/2016
WO WO 2017/007752 A1 1/2017

OTHER PUBLICATIONS

International Search Report and Written Opinion dated Jun. 13, 2019 for International Application No. PCT/IB2018/060049, 21 pages.

*Primary Examiner* — Amanda Lauritzen Moher
*Assistant Examiner* — Jillian K. McGough
(74) *Attorney, Agent, or Firm* — Frost Brown Todd LLC

(57) ABSTRACT

An apparatus includes a processing assembly, a plurality of field generators, and a patient tracking assembly. The patient tracking assembly includes a sensor assembly and a communication assembly. The sensor assembly includes a first body, a first sensor, and an electrical conduit. The first body selectively attaches to a patient. The first sensor is mounted to the first body and generates a signal in response to movement within an electromagnetic field. The communication assembly includes a second body and a cable. The second body rotates relative to the first body from a first rotational position to a second rotational position. The cable extends away from the second body. The cable communicates with the processing assembly. The electrical conduit couples the first sensor with the cable while the casing is in the first rotational position and the second rotational position.

20 Claims, 15 Drawing Sheets

(51) Int. Cl.
- *A61B 5/06* (2006.01)
- *A61B 1/233* (2006.01)
- *A61B 17/24* (2006.01)
- *A61B 90/00* (2016.01)
- *A61M 25/01* (2006.01)
- *A61M 25/10* (2013.01)
- *A61M 25/09* (2006.01)
- *A61B 17/00* (2006.01)
- *A61B 1/00* (2006.01)
- *A61B 1/01* (2006.01)
- *H02G 11/02* (2006.01)
- *A61B 34/00* (2016.01)
- *A61M 29/02* (2006.01)
- *A61M 25/00* (2006.01)

(52) U.S. Cl.
CPC .......... *A61B 5/6833* (2013.01); *A61B 5/6851* (2013.01); *A61B 5/6852* (2013.01); *A61B 5/6891* (2013.01); *A61B 17/24* (2013.01); *A61B 90/361* (2016.02); *A61M 25/0105* (2013.01); *A61M 25/1018* (2013.01); *A61B 1/00082* (2013.01); *A61B 1/00133* (2013.01); *A61B 1/00147* (2013.01); *A61B 1/01* (2013.01); *A61B 34/25* (2016.02); *A61B 90/37* (2016.02); *A61B 2017/00477* (2013.01); *A61B 2034/2051* (2016.02); *A61B 2034/2072* (2016.02); *A61B 2090/3975* (2016.02); *A61B 2217/007* (2013.01); *A61M 25/0113* (2013.01); *A61M 25/09041* (2013.01); *A61M 29/02* (2013.01); *A61M 2025/0002* (2013.01); *H01R 2201/12* (2013.01); *H02G 11/02* (2013.01)

(58) Field of Classification Search
CPC ....... A61B 1/233; A61B 5/062; A61B 5/6891; A61B 90/361; A61B 2034/2051; A61B 1/00133; A61B 1/00082; A61B 2090/3975; A61B 1/01; A61B 1/00147; A61B 2017/00477; A61B 2217/007; A61B 2034/2072; A61B 90/37; A61B 34/25; A61M 25/1018; A61M 25/0105; A61M 25/0113; A61M 25/09041; A61M 2025/0002; A61M 29/02; H02G 11/02; H01R 2201/12

See application file for complete search history.

(56) References Cited

U.S. PATENT DOCUMENTS

| | | | |
|---|---|---|---|
| 7,720,521 B2 | 5/2010 | Chang et al. | |
| 8,123,722 B2 | 2/2012 | Chang et al. | |
| 8,190,389 B2 | 5/2012 | Kim et al. | |
| 8,320,711 B2 | 11/2012 | Altmann et al. | |
| 8,702,626 B1 | 4/2014 | Kim et al. | |
| 8,777,926 B2 | 7/2014 | Chang et al. | |
| 8,947,076 B2* | 2/2015 | Bogos | G01D 5/14 324/207.25 |
| 9,095,646 B2 | 8/2015 | Chow et al. | |
| 9,155,492 B2 | 10/2015 | Jenkins et al. | |
| 9,167,961 B2 | 10/2015 | Makower et al. | |
| 9,198,736 B2 | 12/2015 | Kim et al. | |
| 9,949,004 B2* | 4/2018 | Cohen | A61H 23/0236 |
| 2002/0188174 A1 | 12/2002 | Aizawa et al. | |
| 2003/0163287 A1* | 8/2003 | Vock | G01P 15/18 702/187 |
| 2006/0020187 A1* | 1/2006 | Brister | A61B 5/6848 600/345 |
| 2006/0084867 A1* | 4/2006 | Tremblay | A61B 34/20 600/434 |
| 2006/0211914 A1* | 9/2006 | Hassler, Jr. | A61F 5/0003 600/37 |
| 2007/0208252 A1 | 9/2007 | Makower | |
| 2008/0183128 A1 | 7/2008 | Morriss et al. | |
| 2010/0030031 A1 | 2/2010 | Goldfarb et al. | |
| 2011/0004057 A1 | 1/2011 | Goldfarb et al. | |
| 2011/0060214 A1 | 3/2011 | Makower | |
| 2012/0071857 A1 | 3/2012 | Goldfarb et al. | |
| 2014/0074141 A1 | 3/2014 | Johnson et al. | |
| 2014/0200444 A1 | 7/2014 | Kim et al. | |
| 2014/0364725 A1 | 12/2014 | Makower | |
| 2016/0008083 A1 | 1/2016 | Kesten et al. | |
| 2016/0278692 A1* | 9/2016 | Larson | A61B 5/4884 |
| 2016/0310042 A1 | 10/2016 | Kesten et al. | |
| 2016/0310714 A1 | 10/2016 | Jenkins et al. | |
| 2017/0120020 A1 | 5/2017 | Lin et al. | |
| 2017/0189664 A1* | 7/2017 | Oliverius | A61B 5/6852 |
| 2018/0193098 A1* | 7/2018 | Caluser | A61B 5/7207 |

\* cited by examiner

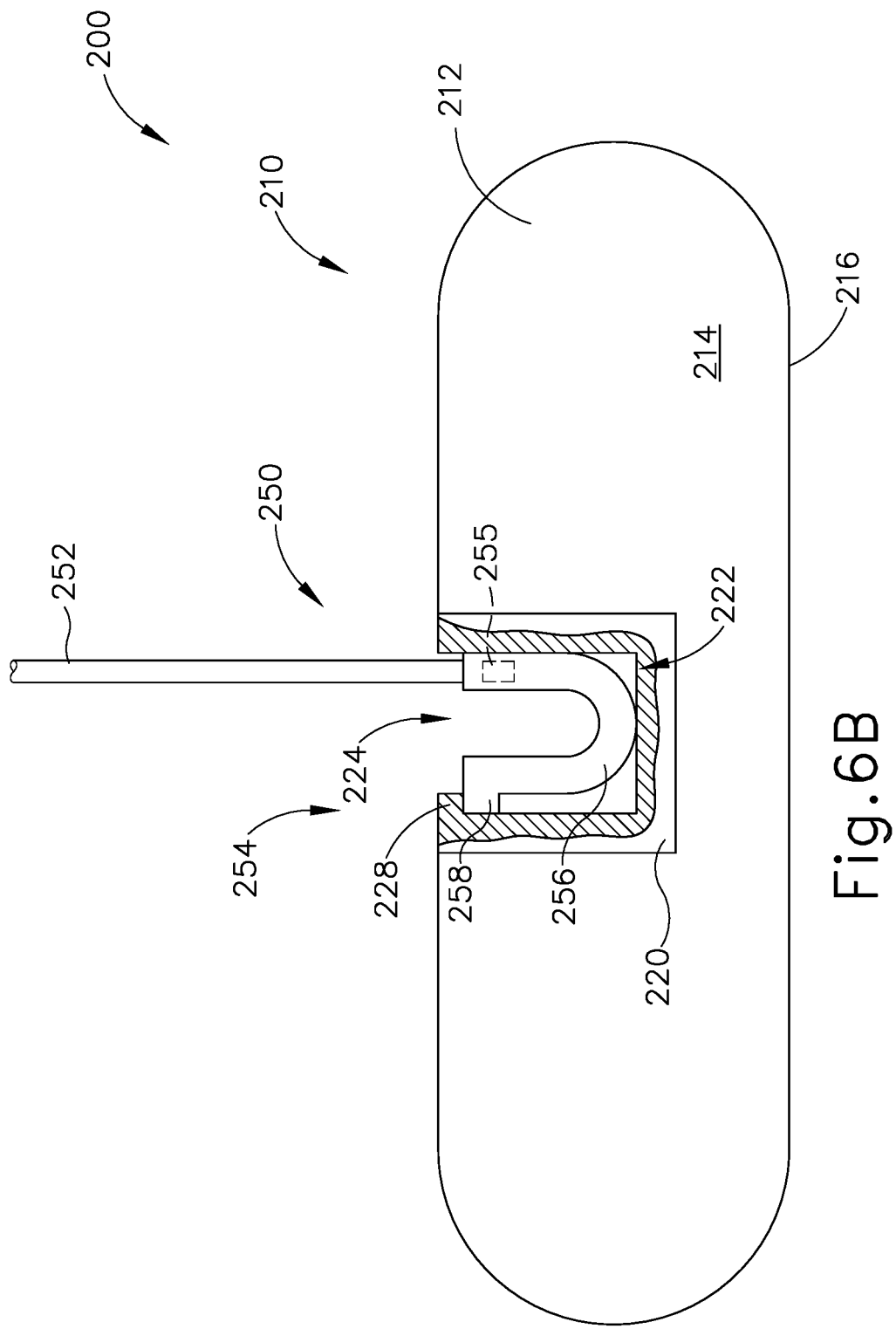

MOUNTED PATIENT TRACKING COMPONENT FOR SURGICAL NAVIGATION SYSTEM

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real-time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Irvine, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 6B depicts a top plan view of the patient tracking assembly of FIG. 5, where the reusable portion is coupled with the disposable portion;

Figure 1A:
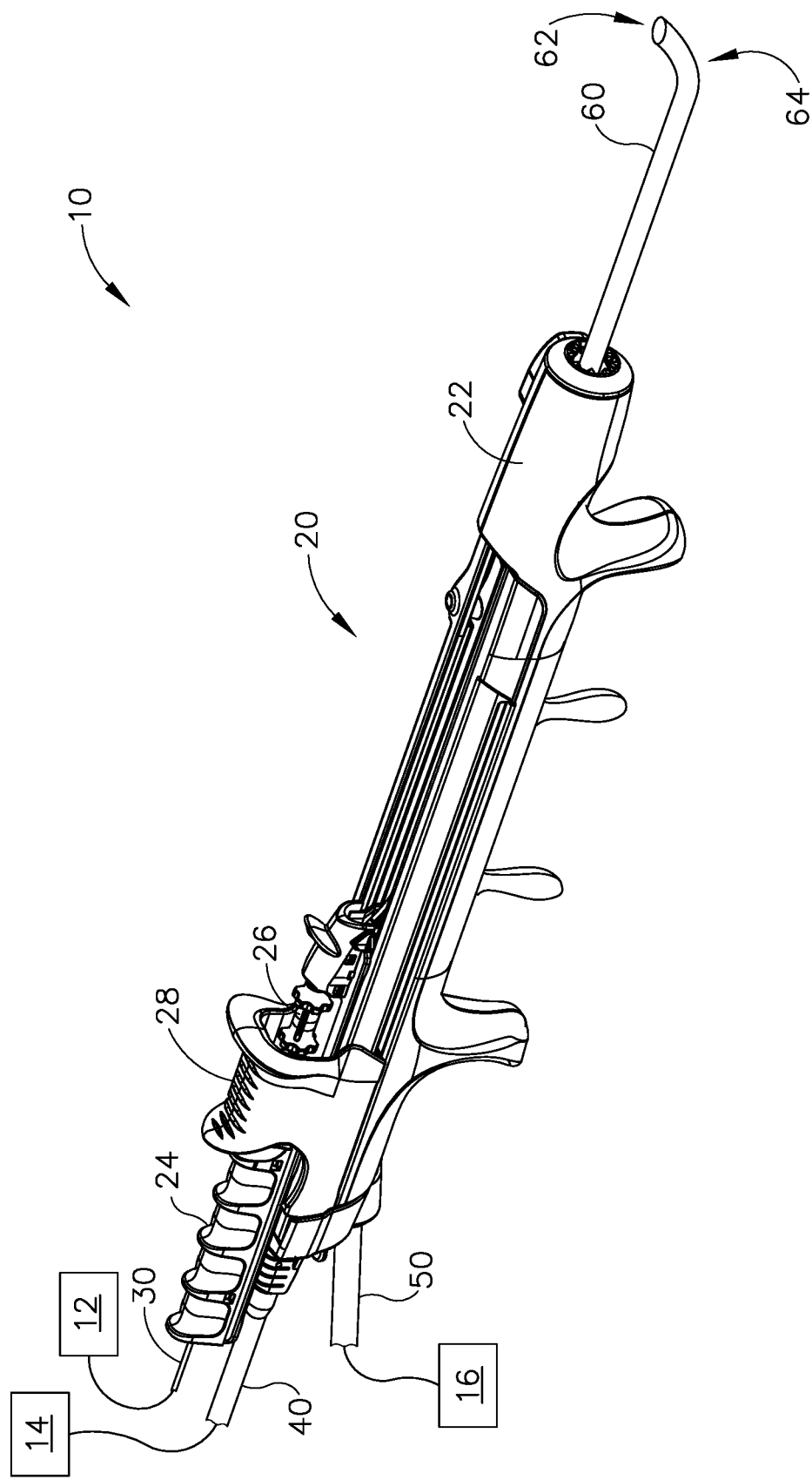
FIG. 1A depicts a perspective view of an exemplary dilation instrument assembly, with a guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows an exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) comprises a source of light. In some other versions, guidewire power source (12) is part of an IGS system as described below. In the present example, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22). Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

B. Exemplary Guidewire

Figure 1B:
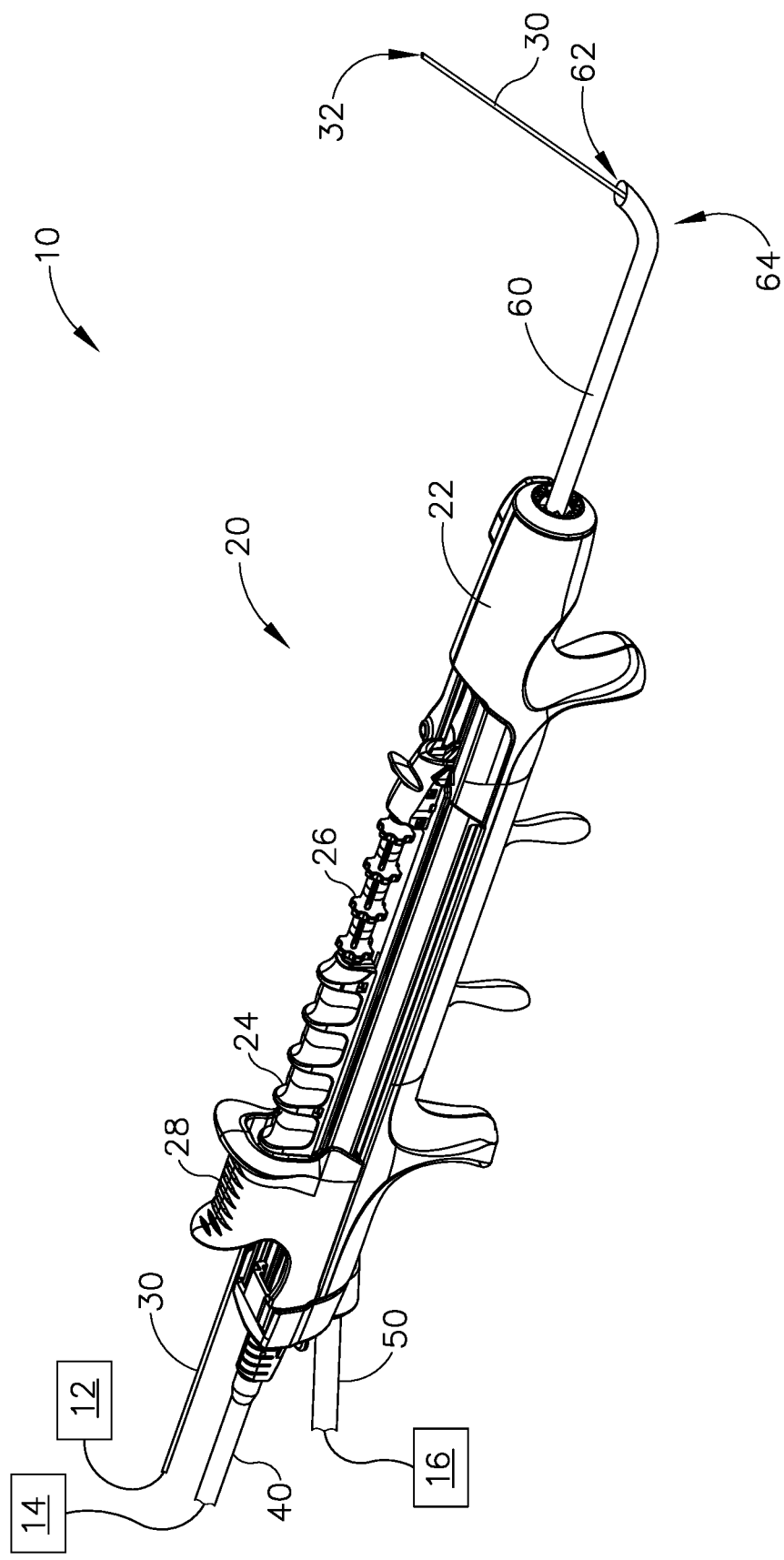
FIG. 1B depicts a perspective view of the dilation instrument assembly of FIG. 1A, with the guidewire in a distal position, and with the dilation catheter in the proximal position.

Dilation instrument (30) further comprises a guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to the distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32). This optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire (30) is configured similar to the Relieva Luma Sentry™ Sinus Illumination System by Acclarent, Inc. of Irvine, Calif. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Figure 1C:
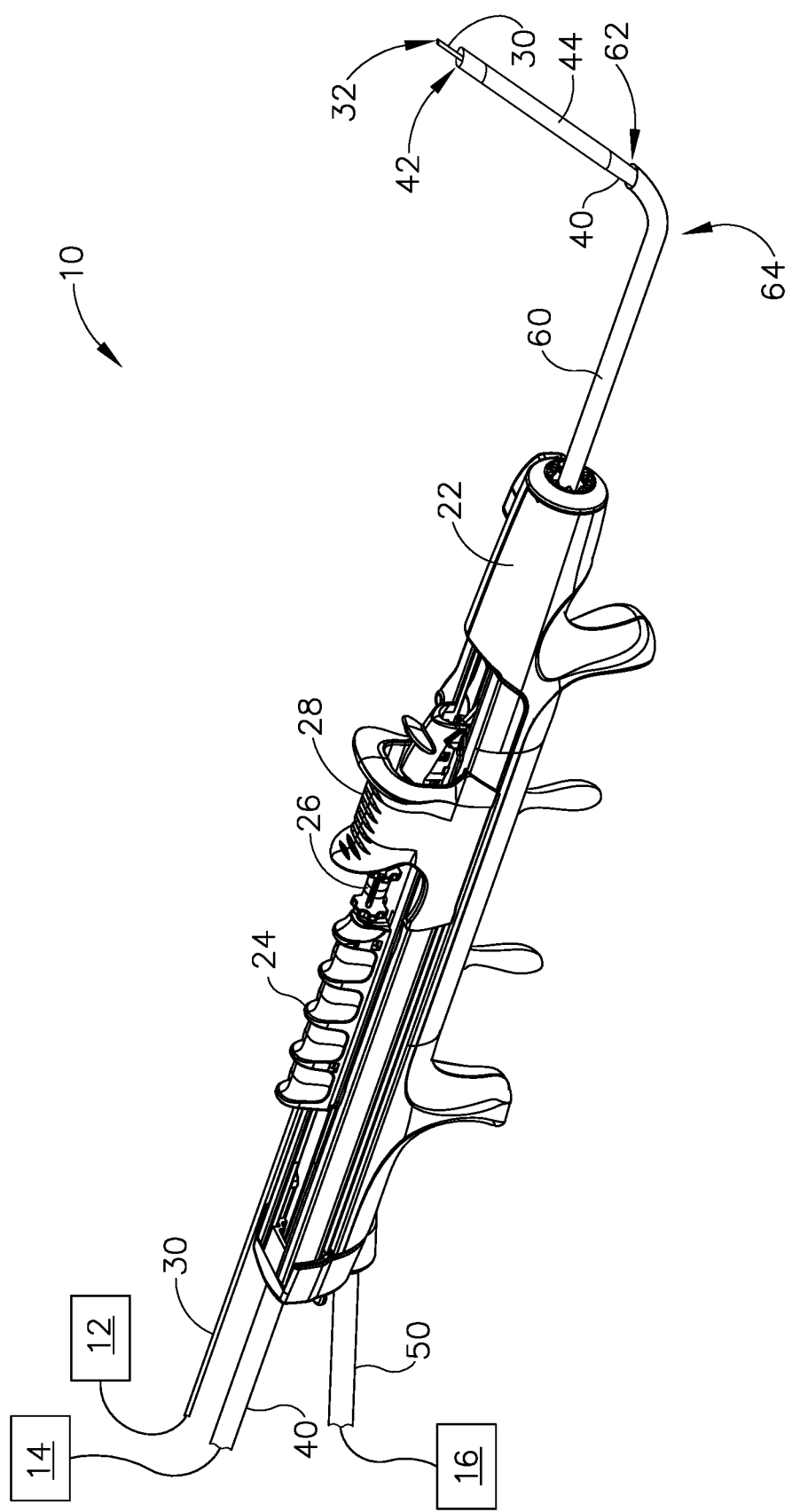
FIG. 1C depicts a perspective view of the dilation instrument assembly of FIG. 1A, with the guidewire in a distal position, with the dilation catheter in a distal position, and with a dilator of the dilation catheter in a non-dilated state.

Dilation instrument (30) further comprises a dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Figure 1D:
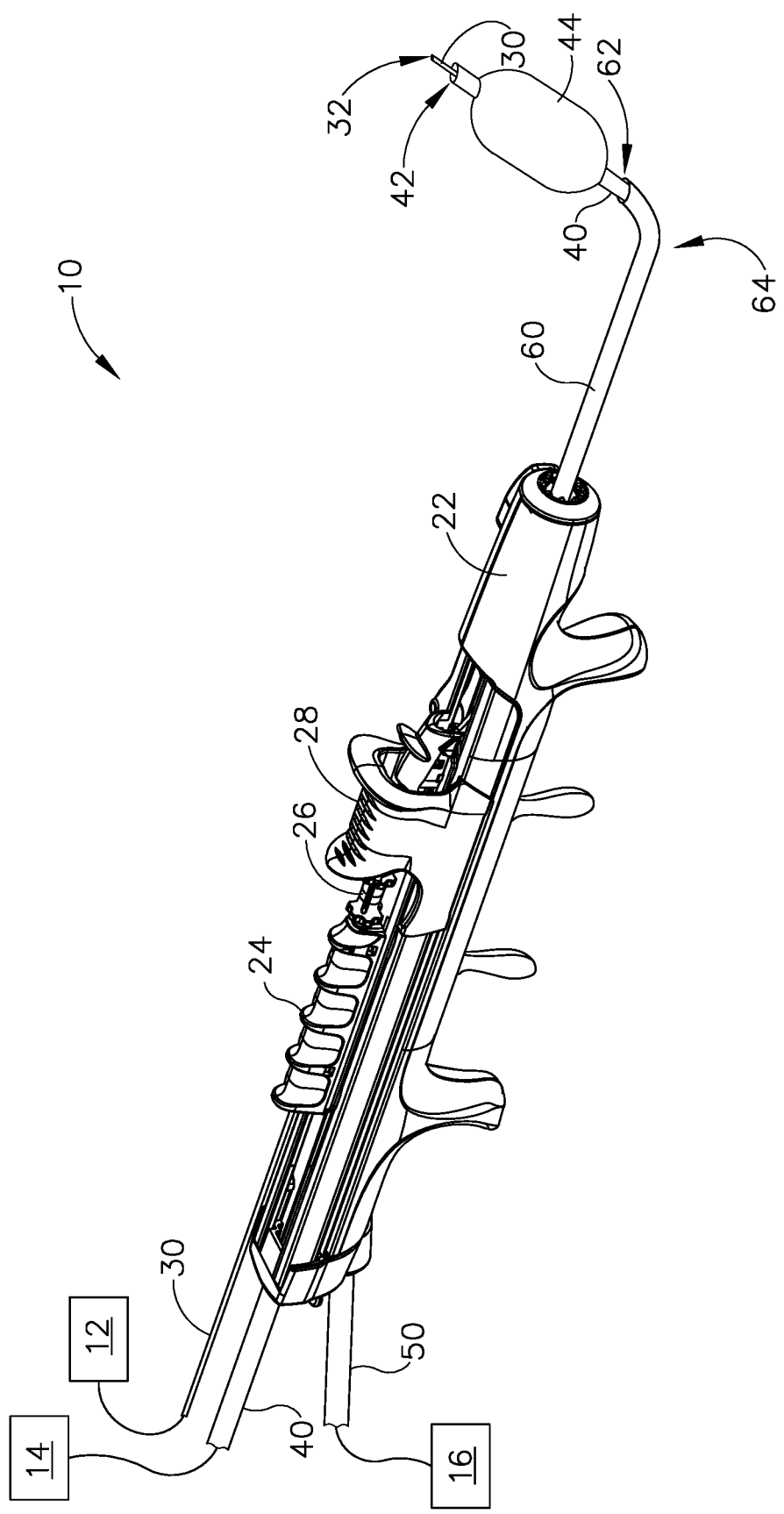
FIG. 1D depicts a perspective view of the dilation instrument assembly of FIG. 1A, with the guidewire in a distal position, with the dilation catheter in the distal position, and with a dilator of the dilation catheter in a dilated state.

Dilation catheter (40) of the present example comprises a non-extensible balloon (44) located just proximal to open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra® Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pat. Pub. No. 2008/0183128, entitled "Methods, Devices and Systems for Treatment and/or Diagnosis of Disorders of the Ear, Nose and Throat," published Jul. 31, 2008, now abandoned. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide member is used to guide guidewire (30) and dilation catheter (40). In some such versions, guidewire (30) is omitted and dilation catheter (40) is slidably disposed about the exterior of the internal malleable guide member. In some other versions, guidewire (30) is slidably disposed about the exterior of the internal malleable guide member; and dilation catheter (40) is slidably disposed about the exterior of guidewire (30). In still other versions, guidewire (30) is slidably disposed within the interior of the malleable guide member; and dilation catheter (40) is slidably disposed about the exterior of the malleable guide member.

By way of example only, versions of dilation instrument (20) that include a malleable guide member may be constructed and operable in accordance with at least some of the teachings of U.S. Pub. No. 2016/0310714, entitled "Balloon Dilation System with Malleable Internal Guide," published Oct. 27, 2016, issued as U.S. Pat. No. 10,137,285 on Nov. 27, 2018, the disclosure of which is incorporated by reference herein. As another merely illustrative example, versions of dilation instrument (20) that include a malleable guide member may be constructed and operable in accordance with at least some of the teachings of U.S. patent application Ser. No. 14/928,260, entitled "Apparatus for Bending Malleable Guide of Surgical Instrument," filed Oct. 30, 2015, issued as U.S. Pat. No. 10,137,286 on Nov. 27, 2018, the disclosure of which is incorporated by reference herein; and/or U.S. Pub. No. 2012/0071857, entitled "Methods and Apparatus for Treating Disorders of the Sinuses," published Mar. 22, 2012, now abandoned, the disclosure of which is incorporated by reference herein.

It should be understood that the variations of dilation instrument (20) described below in the context of an IGS system may be incorporated into versions of dilation instrument (20) having a malleable guide just like the variations of dilation instrument (20) described below in the context of an IGS system may be incorporated into versions of dilation instrument (20) having a rigid guide catheter (60).

Various examples below describe the use of an IGS system to provide navigation of instruments within a patient. In particular, various examples below describe how dilation instrument assembly (10) may be modified to incorporate IGS system features. However, it should also be understood that dilation instrument assembly (10) may be used in conjunction with conventional image guidance instruments, in addition to being used with IGS system components. For instance, dilation instrument assembly (10) may be used in conjunction with an endoscope, at least to provide initial positioning of guide catheter (60) in a patient. By way of example only, such an endoscope may be configured in accordance with at least some of the teachings of U.S. Pub. No. 2010/0030031, now abandoned, the disclosure of which is incorporated by reference herein. Other suitable kinds of endoscopes that may be used with the various versions of dilation instrument assembly (10) described herein will be apparent to those of ordinary skill in the art.

Other exemplary dilation catheter systems that may be used include the systems described in U.S. Pat. Nos. 8,777,926 and 9,095,646, the disclosures of which are incorporated by reference herein; and the Relieva Ultirra® Sinus Balloon Catheter system by Acclarent, Inc. of Irvine, Calif.

II. Exemplary Image Guided Surgery Navigation System

Figure 2:
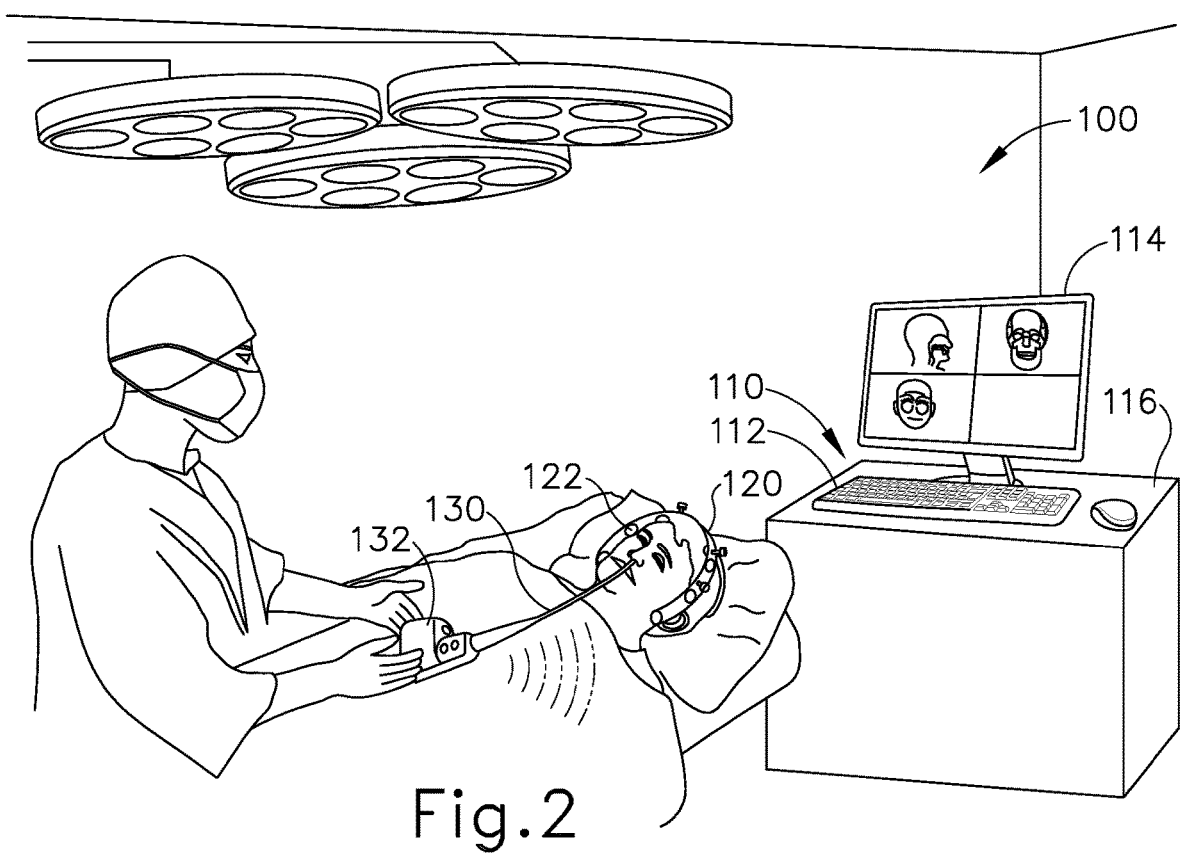
FIG. 2 depicts a schematic view of an exemplary sinus surgery navigation system.

FIG. 2 shows an exemplary IGS navigation system (100) whereby an ENT procedure may be performed using IGS. In some instances, IGS navigation system (100) is used during a procedure where dilation instrument assembly (10) that may be used to dilate the ostium of a paranasal sinus; or to dilate some other anatomical passageway (e.g., within the ear, nose, or throat, etc.). However, it should be understood that IGS navigation system (100) may be readily used in various other kinds of procedures.

In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

Figure 3:
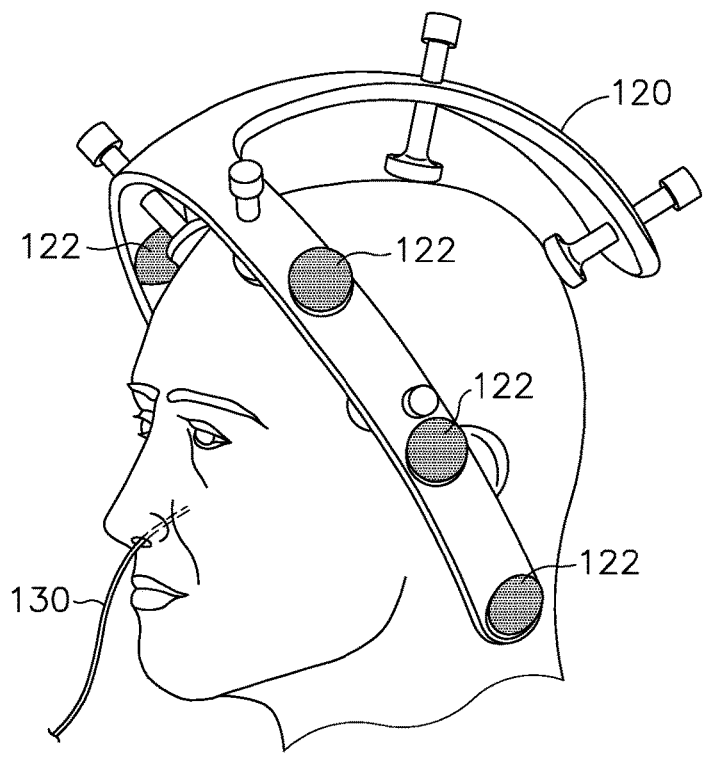
FIG. 3 depicts a perspective view of the head of a patient, with components of the navigation system of FIG. 2.

IGS navigation system (100) of the present example comprises a set of magnetic field generators (122). Before a surgical procedure begins, field generators (122) are fixed to the head of the patient. As best seen in FIG. 3, field generators (122) are incorporated into a frame (120), which is clamped to the head of the patient. While field generators (122) are secured to the head of the patient in this example, it should be understood that field generators (122) may instead be positioned at various other suitable locations and on various other suitable structures as will be described in greater detail below. By way of example only, field generators (122) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130) that is inserted into a nasal sinus of the patient and in other locations within the patient's head. Various suitable components that may be used to form and drive field generators (122) will be apparent to those of ordinary skill in the art in view of the teachings herein.

Navigation guidewire (130) may be used as a substitute for guidewire (30) described above, and may include a sensor (not shown) that is responsive to movement within the fields generated by field generators (122). In particular, signals generated by the sensor of navigation guidewire (130) may be processed by processor (110) to determine the three-dimensional location of navigation guidewire (130) within the patient. Various suitable forms that the sensor may take will be apparent to those of ordinary skill in the art in view of the teachings herein, particularly in view of several of the references that are cited herein in the context of IGS navigation system (100). It should be understood that, when used as a substitute for guidewire (30) in dilation instrument assembly (10), navigation guidewire (130) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like the sensor of navigation guidewire (130), including but not limited to the exemplary dilation catheter (40) described above.

IGS navigation system (100) of the present example further comprises a processor (110), which controls field generators (122) and other elements of IGS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 2 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three-dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

In the present example, navigational guidewire (130) includes one or more coils at the distal end of navigational guidewire (130). Such a coil serves as a sensor as referred to above. When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (100) to determine the location of the distal end of navigational guidewire (130) within a three-dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three-dimensional model of the anatomy within and adjacent to the patient's nasal cavity; in addition to being used to provide navigation for dilation catheter system (100) within the patient's nasal cavity. Alternatively, any other suitable device may be used to generate a three-dimensional model of the anatomy within and adjacent to the patient's nasal cavity before navigational guidewire (130) is used to provide navigation for dilation catheter system (100) within the patient's nasal cavity. By way of example only, a model of this anatomy may be generated in accordance with at least some of the teachings of U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

III. Exemplary Support Assembly for Navigation System Components

Some medical procedures, including but not limited to medical procedures that are performed in the ear, nose, or throat of a patient (referred to herein as "ENT procedures"), may be performed while the patient is supported by a chair. As shown in FIGS. 2-3, when an ENT procedure is performed with the assistance of an IGS navigation system (100), it may be necessary to position an array of field generators (122) around the patient's head. In the example described above, field generators (122) are mounted to a frame (120), which is mounted to the patient's head. In this arrangement, when the head of the patient moves, frame (120) and field generators (122) move with the head of the patient, such that the electromagnetic field generated by field generators (122) also moves with the head of the patient. Thus, the frame of reference for IGS navigation system (100) will move with the head of the patient, such that patient head movement will not negatively impact the position data indicating the position of navigational guidewire (130) relative to the head of the patient.

In some instances, it may be desirable to instead position field generators (122) on a support structure that is not mounted to the patient's head. For instance, when the patient is seated in a chair, it may be desirable to have the field generators (122) supported by the structure of the chair rather than being supported by the patient's head. However, mounting field generators (122) to a support structure that is secured to a chair may present other issues that may need to be addressed.

Conventional medical procedure chairs, including those designed particularly for use in ENT procedures, may include several metallic components in the headrest of the chair. While such headrests may provide adequate structural support for field generators (122), metallic components in such headrests (and/or elsewhere within the chair) may interfere with the functioning or accuracy of IGS navigation system (100) if the metallic components are too close to field generators (122). It may therefore be desirable to rely on the chair to structurally support field generators (122) while avoiding the risk of metallic features of the chair compromising the functioning or accuracy of IGS navigation system (100).

The following example relates to a support assembly (500) relying on the chair itself (rather than the patient's head) to structurally support IGS navigation system (100) components such as field generators (122), without the risk of any metallic components of the chair interfering with the functioning or accuracy of IGS navigation system (100).

Figure 4:
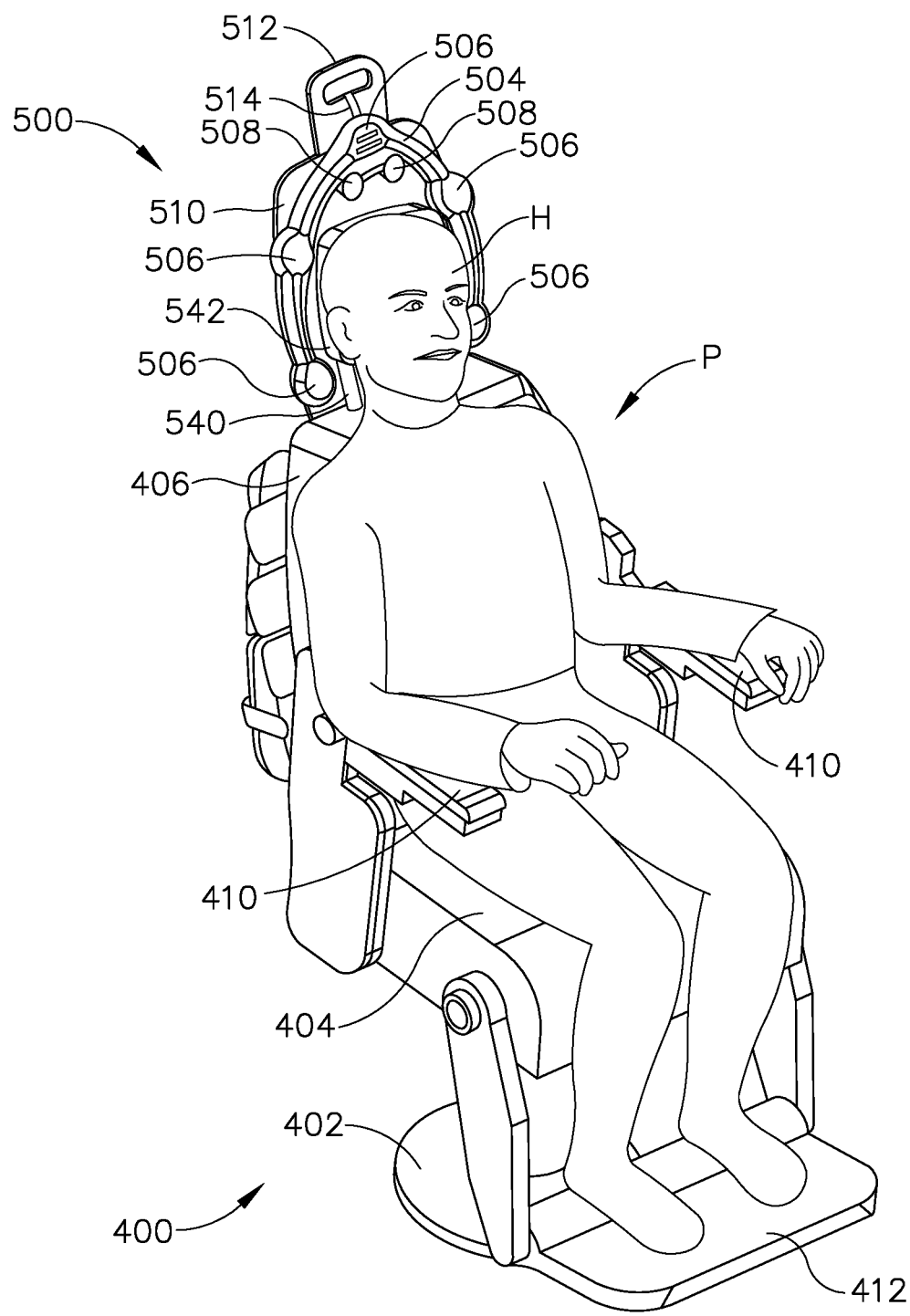
FIG. 4 depicts a front perspective view of an exemplary medical procedure chair, with an exemplary navigation component support assembly secured to the chair, and with a representation of a patient seated in the chair.

FIG. 4 shows an exemplary support assembly (500) mounted to an exemplary ENT procedure chair (400). Exemplary support assembly (500) includes a plurality of field generators (506) may be readily incorporated into IGS navigation system (100) in replacement of frame (120) and field generators (122). Therefore, field generators (506) may function substantially similar to field generators (122) described above, with differences elaborated below. As will be described in greater detail below, field generators (506) are attached to a frame (504), which is further fixable to chair (400), such that field generators (506) are fixed relative to chair (400) during exemplary use. Chair (400) of this example includes a base (402), a bottom support (404), a backrest (406), a pair of armrests (410), and a footrest (412). In this particular example, chair (400) lacks a headrest. In some scenarios, a headrest of chair (400) may be removed to accommodate support assembly (500). Backrest (406) is configured to pivot relative to bottom support (404) in order to achieve various recline angles.

Support assembly (500) of this example includes a housing (510). A post (540) extends upwardly from backrest (406) to support housing (510). While in the current example, post (540) acts to couple support assembly (500) to chair (400), any other suitable mechanisms for retrofitting support assembly (500) to chair (400) may be used as would be apparent to one having ordinary skill in the art in view of the teachings herein. For example, chair (400) may be configured according to one or more teachings of U.S. Patent App. No. 62/555,824, entitled "Apparatus to Secure Field Generating Device to Chair," filed Sep. 8, 2017, the disclosure of which is incorporated by reference herein.

A frame (504) is secured to the front of housing (510). Frame (504) is generally shaped like a horseshoe in this example and includes a plurality of integral field generators (506). A pair of securing features (508) secure frame (504) to housing (510), while a headrest (542) is also secured to housing (510). Headrest (542) is configured to support the head (H) of a patient (P) while the patient (P) is seated on bottom support (404). Frame (504) is configured to hold field generators (506) in a generally horseshoe-shaped arrangement about the head (H) of the patient (P), without frame (504) contacting the head (H) of the patient (P).

A handle (512) is configured to be grasped by an operator to position frame (504), field generators (506), and headrest (542) relative to post (540). A knob or plurality of knobs (not shown) may be rotated to selectively lock and unlock the vertical and/or the lateral position of frame (504), field generators (506), and headrest (542) relative to post (540) and chair (400). Therefore, an operator may adjust the positioning of support assembly (500) relative to chair (400) before an exemplary procedure in order to properly position support assembly (500) for a specific patient.

A cable (514) is in communication with field generators (506) in order to provide a conduit for communication between field generators (506) and processor (110) of IGS navigation system (100). Field generators (506) of this example are configured and operable just like field generators (122) described above, except that field generators (506) are fixed relative to support assembly (500) rather than relative to the head of the patient. Therefore, field generators (506) are operable to generate an electromagnetic field around the head (H) of the patient (P) while the head (H) is supported by headrest (542). Processor (110) may drive field generators (506). In particular, field generators (506) are operable to transmit alternating magnetic fields of different frequencies into a region in proximity to frame (504). Similar to field generators (122) described above, field generators (506) thereby enable tracking of the position of navigation guidewire (130), or any other instrument with a suitable sensor, that is inserted into a nasal sinus of the patient (P) and in other locations within the head (H).

Similar as to when processor (110) and display screen (114) are used with field generators (122) described above, processor (110) and display screen (114) may provide video in real time via display screen (114) showing the position of the distal end of navigational guidewire (130) in relation to a video camera image of the patient's head, a CT scan image of the patient's head, and/or a computer generated three-dimensional model of the anatomy within and adjacent to the patient's nasal cavity.

IV. Exemplary Patient Tracking Sensor Assemblies

When field generators (506) are in fixed positions relative to chair (400) during exemplary use, rather than being in fixed positions relative to head (H) of patient (P), the frame of reference for IGS navigation system (100) (i.e., the electromagnetic field generated by field generators (506)) does not move with the head (H) of the patient (P). In some instances, a procedure may involve intentional or inadvertent movements by the patient (P) while situated in chair (200), such that the patient's head (H) may shift positions, location, and/or orientation in relation to support assembly (500). When a navigation guidewire (130) (or other instrument having a sensor compatible with IGS navigation system (100)) is disposed in the head (H) of the patient (P), IGS navigation system (100) may not be able to differentiate between (i) movement of navigation guidewire (130) relative to the head (H) of the patient and (ii) movement of the head (H) of the patient (P) with navigation guidewire (130) (e.g., when navigation guidewire (130) remains stationary relative to the head (H) of the patient (P) yet moves relative to the head (H) of the patient (P)). Thus, by not securing field generators (506) relative to the head (H) of the patient (P), IGS navigation system (100) may provide inaccurate position data relative to the head (H) of the patient (P) when the head (H) of the patient (P) moves while navigation guidewire (130) is disposed in the head (H) of the patient (P). It may therefore be desirable for IGS navigation system (100) include features and functionality to account for movement of the patient's head (H), to preserve the accuracy of IGS navigation system (100).

For instance, it may beneficial to incorporate navigation system components, such as sensors, onto a patient's head (H) that are configured to generate signals in response to movement within the field generated by field generators (506), and communicate such signals to IGS navigation system (100), such that movement of a patient's head (H) may be separately tracked and thereby accounted for by IGS navigation system (100). It may further be desirable for a sensor that is dedicated to tracking patient head (H) movement to be unobtrusive, and particularly less obtrusive than frame (120). Less intrusive means of attaching navigation system components onto a patient's head may be beneficial for ease in installation and enhanced comfort for the patient during the procedure.

The following description provides examples of a navigation system component in the form of a patient tracking device that is configured to cooperatively communicate with IGS navigation system (100) to improve accuracy in tracking the position of an instrument (e.g., navigation guidewire (130)) that is inserted into the patient's head (H). In particular, the patient tracking device is configured to be responsive to movement of a patient's head (H) in relation to the fields generated by field generators (506), such that the signals generated by a navigational instrument (e.g., navigation guidewire (130)) may be processed by processor (110) through an error correction algorithm, to effectively subtract-out patient head (H) movement, to thereby accurately determine the three-dimensional location of the navigational instrument within the head (H) of the patient (P).

It should be understood that the patient tracking devices described below may be readily incorporated into any of the various navigation systems (100) and support assemblies (500) described above and in any of the various medical procedures described in the various references described herein. Other suitable ways in which the below-described patient tracking devices may be used will be apparent to those of ordinary skill in the art in view of the teachings herein.

A. Patient Tracking Assembly Having a Disposable Portion and a Reusable Portion

It may be expensive having a patient tracking device that may only be used for one surgical procedure. Therefore, it may be desirable to have a patient tracking device that may at least be partially re-used in multiple surgical procedures. For instance, it may be desirable to use a patient tracking device having a first portion that may be configured for a single use during one surgical procedure; while also having a second portion that may be configured for use in multiple surgical procedures. This may reduce the cost per procedure of using a patient tracking device in conjunction with IGS navigation system (100).

Figure 5:
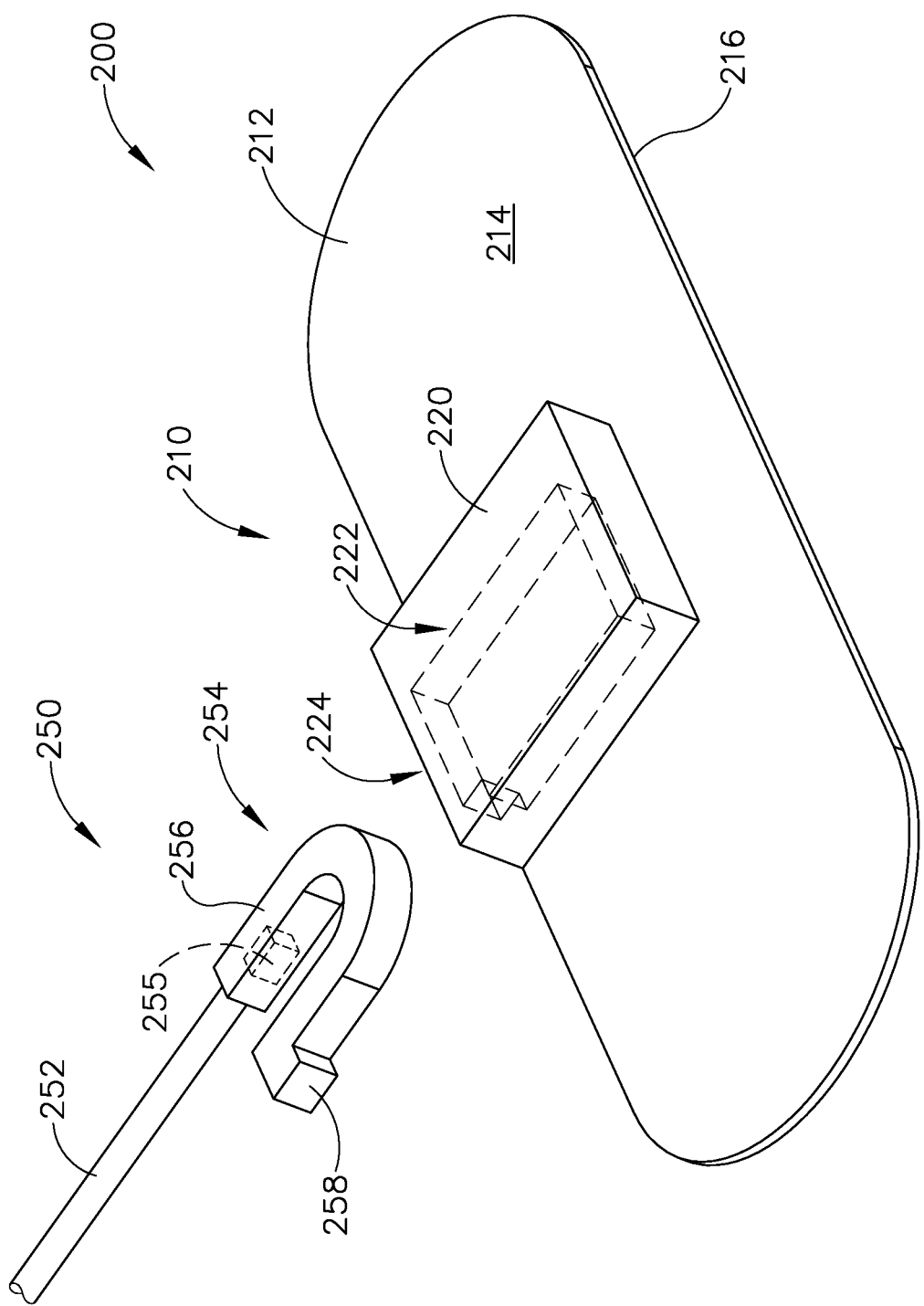
FIG. 5 depicts a perspective view of an exemplary patient tracking assembly having a disposable portion and a reusable portion.

FIGS. 5-6B show a patient tracking assembly (200) that may be readily incorporated into IGS navigation system (100) where field generators (506) are not fixed to head (H) of patient (P). As will be described in greater detail below, patient tracking assembly (200) includes a disposable portion (210) and a reusable portion (250). As will also be described in greater detail below, disposable portion (210) is configured to attach to head (H) of patient and selectively couple with reusable portion (250) such that reusable portion (250) is fixed relative to head (H) of patient (P) during exemplary use; while reusable portion (250) is configured to communicate with processor (110) in order to track the position of head (H) of patient (P) relative to field generators (506) during exemplary use.

Disposable portion (210) includes a flexible adhesive pad (212) and a coupling block (220). Flexible adhesive pad (212) includes a top surface (214) and a bottom adhesive surface (216). Coupling block (220) is attached to, and extends away from, top surface (214) of pad (212). Coupling block (220) may attach to pad (212) using any suitable technique as would be apparent to one having ordinary skill in the art in view of the teachings herein.

Bottom adhesive surface (216) includes an adhesive material that is configured to suitably attach disposable portion (210) to head (H) of patient (P) such that disposable portion (210) does not move relative to head (H) of patient (P) during exemplary use. Prior to a surgical procedure, an operator may attach disposable portion (210) to head (H) of patient (P) via bottom adhesive surface (216). While in the current example, flexible adhesive pad (212) is being secured to head (H) of patient (P), pad (212) may couple with any other suitable location on patient (P) as would be apparent to one having ordinary skill in the art in view of the teachings herein, particularly when navigation guidewire (130) or some other navigation-enabled instrument is inserted into a patient (P) in a location other than the head (H). Bottom adhesive surface (216) may include any suitable adhesive material that would be apparent to one having ordinary skill in the art in view of the teachings herein, such as a pressure sensitive adhesive. Bottom adhesive surface (216) may be originally covered by a suitable sheathing material such that surface (216) does not unintentionally attach to any object before intended use of disposable portion (210). After a surgical procedure is completed, an operator may peel pad (212) off head (H) of patient (P), thereby overcoming the adhesive connection between pad (212) and head (H).

Figure 6A:
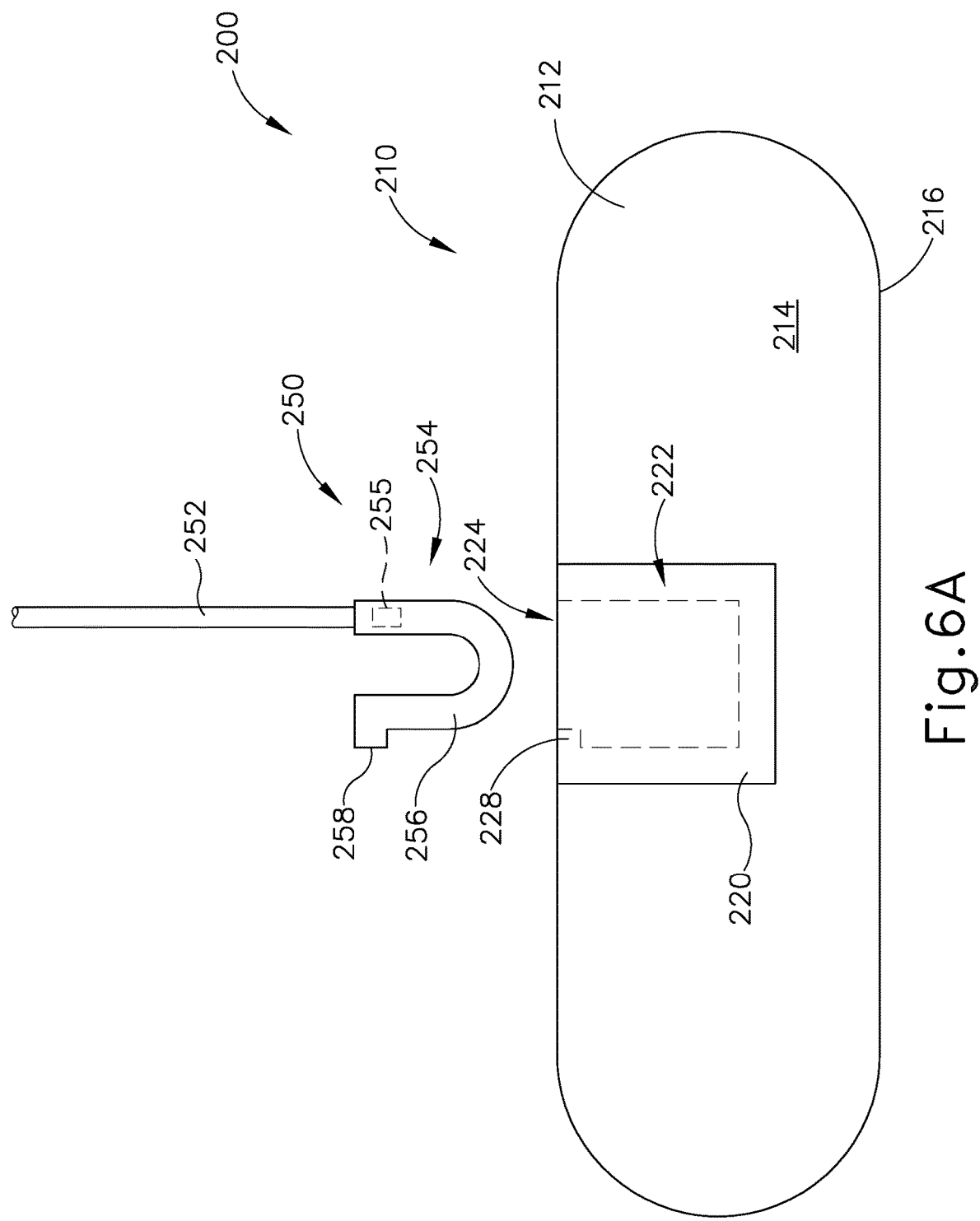
FIG. 6A depicts a top plan view of the patient tracking assembly of FIG. 5, where the reusable portion is decoupled from the disposable portion.
Figure 7:
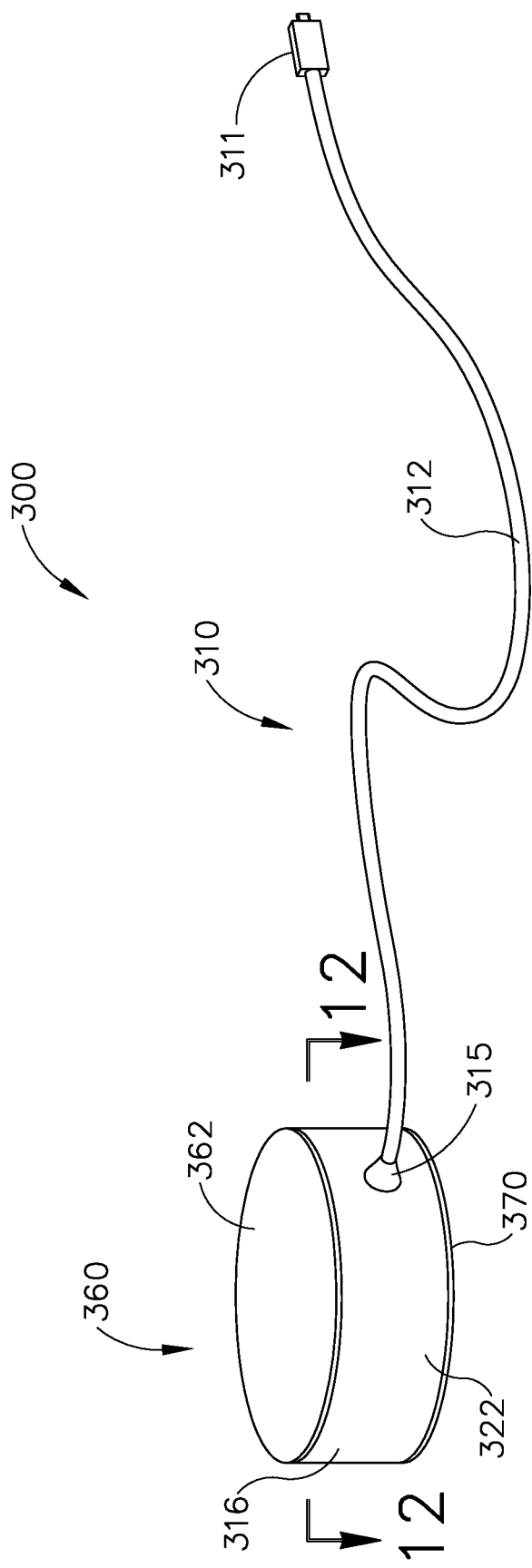
FIG. 7 depicts a perspective view of another exemplary patient tracking device.
Figure 8:
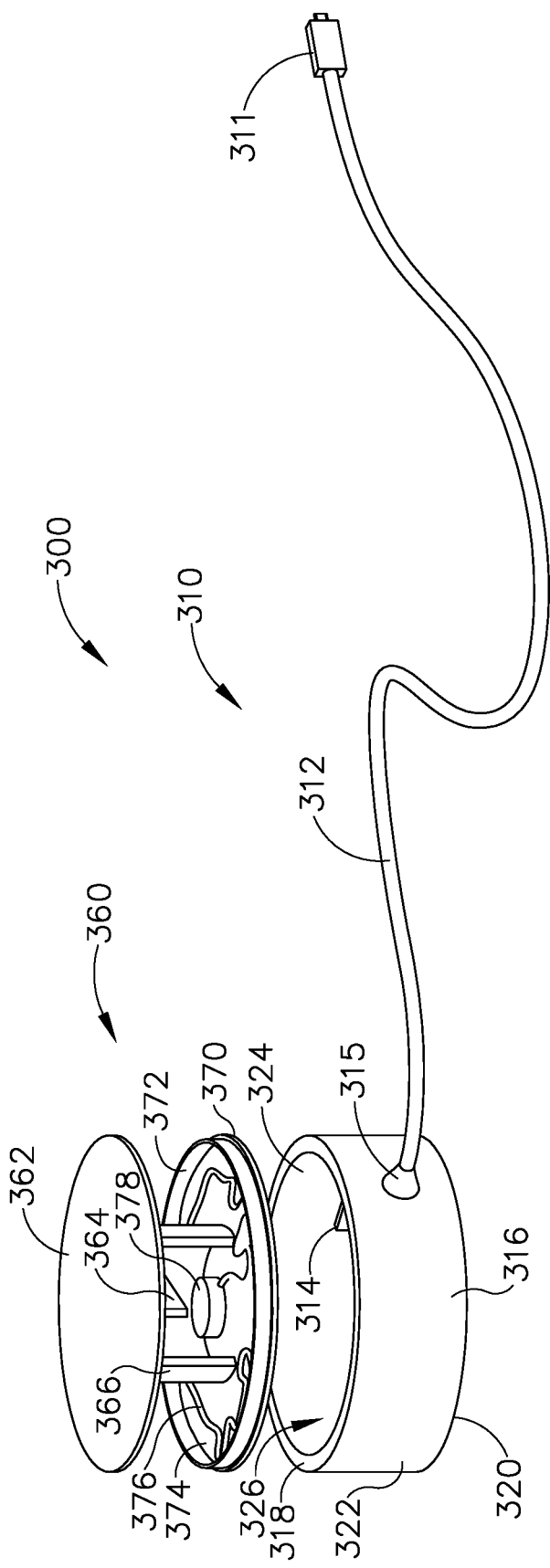
FIG. 8 depicts an exploded perspective view of the patient tracking device of FIG. 7.
Figure 9:
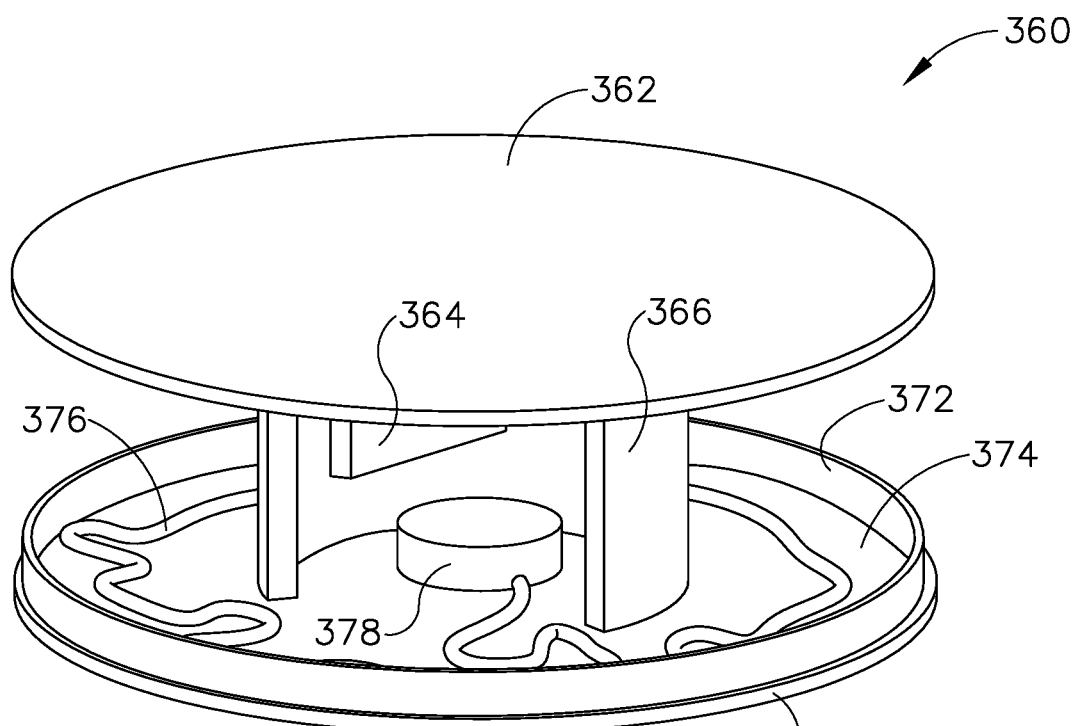
FIG. 9 depicts a perspective view of a sensor assembly of the patient tracking device of FIG. 7.
Figure 10:
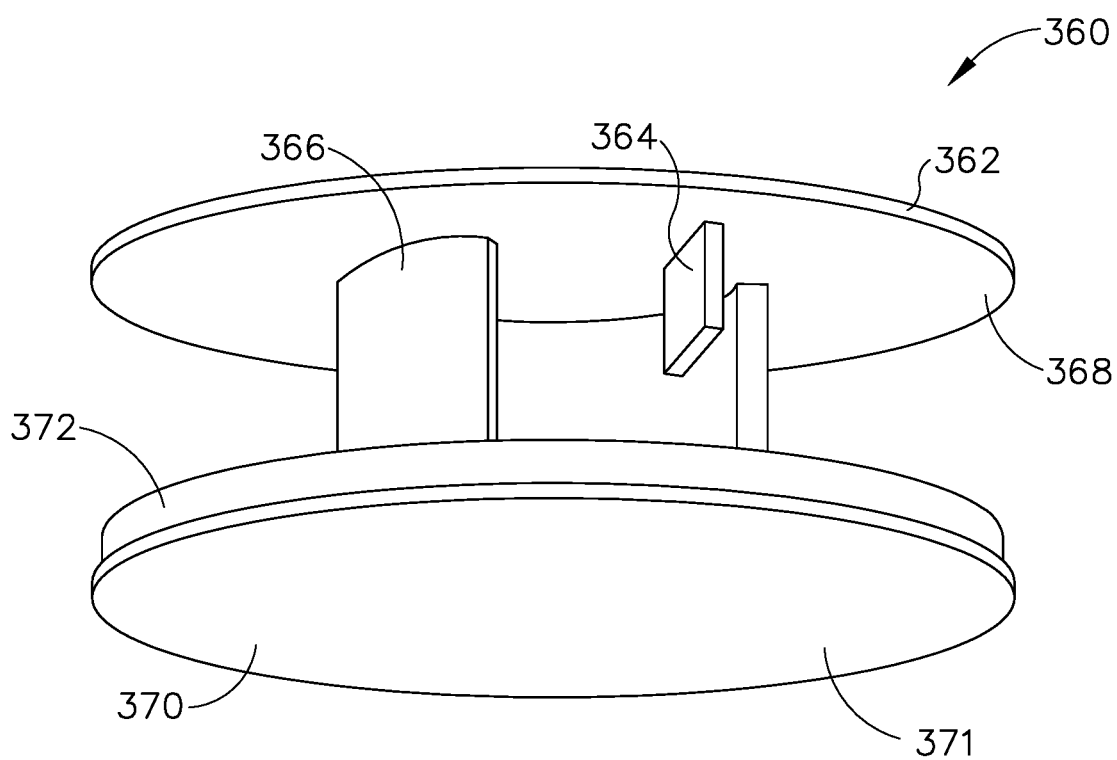
FIG. 10 depicts another perspective view of the sensor assembly of FIG. 9.

Coupling block (220) is configured to selectively couple with reusable portion (250). Coupling block (220) defines an opening (224) on the exterior of coupling block (220) which extends into a housing recess (222) located within the interior of coupling block (220). In addition, as best seen in FIGS. 6A-6B, coupling block (220) includes a protrusion (228) located within housing recess (222). As will be described in greater detail below, opening (224) and housing recess (222) are dimensioned to receive a coupling assembly (254) of reusable portion (250), while protrusion (228) may interact with coupling assembly (254) of reusable portion (250) such that reusable portion (250) may not accentually disassociate with coupling block (220) during exemplary use. In other words, coupling block (220) is configured to selectively couple with coupling assembly (254) of reusable portion (250).

Reusable portion (250) includes a cable (252) extending proximally from coupling assembly (254), and a sensor (255). As will be described in greater detail below, when properly coupled with disposable portion (210), sensor (255) may be utilized with processor (110) to determine the location of head (H) relative to field generators (506), such that processor (110) may accurately display the location of navigation guidewire (130) (or any other suitable instrument) within head (H) of patient (P) during exemplary use.

Cable (252) is configured to provide a conduit for communication between sensor (255) and processor (110) during exemplary use. Therefore, cable (252) may directly connect with console (116) such that sensor (255) is in wired communication with processor (110) via cable (252). Alternatively, cable (252) may connect sensor (255) with a wireless communication device that is in wireless communication with console (116), similar to how coupling unit (132) establishes wireless communication between navigation guidewire (130) and console (116). Cable (252) may provide a conduit for communication between sensor (255) and processor (110) through any suitable techniques known to one having ordinary skill in the art in view of the teachings herein.

As mentioned above, and as will be described in greater detail below, coupling assembly (254) is dimensioned to be inserted within opening (224) and housing recess (222) of coupling block (220) in order to selectively couple coupling assembly (224) with reusable portion (250). It should be understood that when coupling assembly (254) is attached to coupling block (220), and when disposable portion (210) is effective fixed to head (H), coupling assembly (254) is effective fixed to head (H) of patient (P).

Coupling assembly (254) includes a resilient U-shaped body (256) and a latch (258). As seen between FIGS. 6A-6B, a distal end of U-shaped body (256) may be inserted through opening (224) such that U-shaped body (256) is within housing recess (222). Protrusion (228) and latch (258) may make contact while U-shaped body (256) is being inserted such that legs of U-shaped body (256) deflect inward toward each other. Once latch (258) is inserted past protrusion (228), as shown in FIG. 6B, legs of U-shaped body (256) may deflect outward due to the resilient nature of U-shaped body (256). Therefore, latch (258) and protrusion (228) may interact with each other such that coupling assembly (254) may not be removed from housing recess (222), effectively fixing coupling assembly (254) within coupling block (220).

After exemplary use, an operator may desire to remove reusable portion (250) from disposable portion (210). Therefore, an operator may deflect legs of U-shaped body (256) inwardly such that latch (258) does not abut against protrusion (228), and pull coupling assembly (254) away from coupling block (220) to remove coupling assembly (254) from the confines of housing recess (222). Reusable portion (250) may then be reused during a different surgical procedure with a new disposable portion (210).

While in the current example, coupling assembly (254) is selectively attachable to coupling block (220) via resilient U-shaped body (256), latch (258), and protrusion (228), any other suitable coupling means may be utilized as would be apparent to one having ordinary skill in the art in view of the teachings herein. For example, coupling assembly (254) may be dimensioned for an interference fit within housing recess (222), such that when an operator inserted coupling assembly (254) through opening (224) and within housing recess (222), contact between coupling assembly (254) and the interior of housing recess (222) provides a sufficient frictional breaking force such that coupling assembly (254) is effectively fixed to coupling block (220) during exemplary use.

Sensor (255) is fixedly housed within U-shaped body (256) of coupling assembly (254). Sensor (255) may be substantially similar to sensor (not shown) from navigation guidewire (130) described above, with differences elaborated below. By way of example only, sensor (225) may comprise one or more coils of wire wrapped around one or more respective axes. Sensor (255) may be responsive to movement within fields generated by field generators (506) during exemplary use. Therefore, signals generated by movement of sensor (255) may be sent to processor (110). Because sensor (255) is attached to coupling block (220) of disposable portion (210) during exemplary use, and because disposable portion (210) is fixed to head (H) of patient (P) in accordance with the description above, signals generated by movement of sensor (255) may be indicative of movement of head (H). Therefore, signals generated by movement of sensor (255) may allow processor (110) to determine the three-dimensional location and orientation of head (H) of patient (P) relative to the plurality of field generators (506) fixed to support assembly (500). Processor (110) may utilize this information, in conjunction with the location of navigation guidewire (130) (or any other suitable instrument) relative to field generators (506), such that processor (110) and display screen (114) may properly display the location of navigation guidewire (130) (or any other suitable instrument) within head (H) of patient (P).

Once a procedure is completed, an operator may remove patient tracking assembly (200) from head (H) of patient (P). An operator may also decouple reusable portion (250) from disposable portion (210) in accordance with the description above, discard disposable portion (210), and keep reusable portion (250) for use in another procedure. Reusable portion (250) may be used for any suitable number of procedures as would be apparent to one having ordinary skill in the art in view of the teachings herein.

B. Patient Tracking Assembly Having Rotatable Communication Assembly

After patient tracking assembly (200) has been attached to the head (H) of a patient (P), it may be desirable to adjust or reorient cable (252) relative to head (H). For instance, in some situations tracking assembly (200) may be initially attached to head (H) in a position where cable (252) becomes an obstruction during an exemplary procedure. If an operator desires to adjust or reorient cable (252) once patient tracking assembly (200) has been attached to patient (P), an operator may have to remove and reattach patient tracking assembly (200) to a position where cable (252) is no longer an obstruction, thereby removing and reapplying flexible adhesive pad (212) to head (H). This may reduce accuracy of patient tracking assembly (200) when used with IGS navigation system (100). Alternatively, an operator may attempt to adjust or reorient cable (252) while patient tracking assembly (200) is still affixed to head (H), which may also reduce accuracy of patient tracking assembly (200).

In addition to an operator attempting to adjust or reorient cable (252) prior to an exemplary operation, patient (P) may move head (H) during an exemplary procedure. Movement of head (H) during an exemplary procedure may bend or pull cable (252) relative to the rest of patient tracking assembly (200), which may also reduce the accuracy of patient tracking assembly (200).

It may be desirable to provide a patient tracking assembly (200) that has a cable configured to rotate around a patient tracking sensor while the patient tracking sensor is attached to patient (P). FIGS. 7-8 and FIGS. 12A-12B show an exemplary patient tracking assembly (300) that provides such functionality. Patient tracking assembly (300) includes a communication assembly (310) and a sensor assembly (360). As will be described in greater detail below, sensor assembly (360) is configured to affix to head (H) of patient (P) such that sensor assembly (360) may accurately track the position of head (H) when used with IGS navigation system (100); while communication assembly (310) is configured rotate relative to sensor assembly (360) during exemplary use while simultaneously communicating data from sensor assembly (360) to console (116).

Sensor assembly (360) includes a cap (362), a base (370), a sensor (378) mounted to base (370), and a service loop (376) in communication with sensor (378). Sensor (378) may be substantially similar to sensor (255) described above, with differences elaborated below. Therefore, sensor (378) may be utilized with processor (110) to determine the location of head (H) relative to field generators (506), such that processor (110) may accurately display the location of navigation guidewire (130) (or any other suitable instrument) within head (H) of patient (P) during exemplary use. While in the present example, sensor (378) is mounted to base (370), sensor (378) may be mounted to any other suitable portion of sensor assembly (360) as would be apparent to one having ordinary skill in the art in view of the teachings herein. For example, sensor (378) may be mounted to cap (362).

Cap (362) and base (370) that connect to each other via a semi-cylindrical shell (366). Semi-cylindrical shell (366) acts as a connecting arm between cap (362) and base (370). Cap (362) includes an interior surface (368) having a first rotation stop (364) extending inwardly toward base (370). When communication assembly (310) and sensor assembly (360) are assembled, first rotation stop (364) is dimensioned to abut against a second rotation stop (314) of communication assembly (310) to limit to rotation of communication assembly (310) relative to sensor assembly (360).

Base (370) includes an exterior surface (371), an interior surface (374), and a circumferential lip (372) extending form interior surface (374) toward cap (362). Exterior surface (371) includes an adhesive material that is configured to suitably attach sensor assembly (360) to head (H) of patient (P) such that sensor assembly (360) does not move relative to head (H) of patient (P) during exemplary use. Prior to a surgical procedure, an operator may attach exterior surface (371) to head (H) of patient (P) via adhesive material when patient tracking assembly (300) is fully assembled. While in the current example, sensor assembly (360) is being secured to head (H) of patient (P), sensor assembly (360) may couple with any other suitable location on patient (P) as would be apparent to one having ordinary skill in the art in view of the teachings herein, particularly when navigation guidewire (130) or some other navigation-enabled instrument is inserted into a patient (P) in a location other than the head (H). Exterior surface (371) may include any suitable adhesive material that would be apparent to one having ordinary skill in the art in view of the teachings herein, such as a pressure sensitive adhesive. Exterior surface (371) may be originally covered by a suitable sheathing material such that exterior surface (371) does not unintentionally attach to any object before intended use of patient tracing assembly (300). After a surgical procedure is completed, an operator may remove patient tracking assembly (30) off head (H) of patient (P), thereby overcoming the adhesive connection between exterior surface (371) and head (H).

Lip (372) is dimensioned to be housed within a casing (316) of communication assembly (310) such that sensor assembly (360) may rotate relative to communication assembly (310). In particular, when sensor assembly (360) is coupled with communication assembly (310), lip (372) is located adjacent to an interior surface (324) of casing (316). Lip (372) and interior surface (324) of casing (316) may abut against each other to laterally constrain sensor assembly (360) relative to casing (316). However, lip (372) and interior surface (324) are dimensioned such that lip (372) may slide along interior surface (324) as sensor assembly (360) rotates relative to communication assembly (310). In other words, the frictional breaking force between lip (372) and interior surface (324) is not so great as to inhibit rotation of sensor assembly (360) relative to casing (316).

As mentioned above, sensor (378) is mounted to interior surface (374) of base (370). Sensor (378) is housed within the confines of semi-cylindrical shell (366). Service loop (376) is in communication with both sensor (378) and cable (312) of communication assembly (310) such that service loop (376) provides a conduit for communication between sensor (378) and cable (312). However, service loop (376) is not fixed to any other portion of sensor assembly (360). Semi-cylindrical shell (366) defines an opening such that service loop (376) may extend from sensor (378) toward cable (312). While in the current example, sensor (378) is located within the confines of semi-cylindrical shell (366), this is optional, as sensor (378) may be fixed to any suitable location on base (370) as would be apparent to one having ordinary skill in the art in view of the teachings herein. Additionally, semi-cylindrical shell (366) may have any suitable geometry to connect cap (362) and base (370) as would be apparent to one having ordinary skill in the art in view of the teachings herein. For example, semi-cylindrical shell (366) may be replaced with a plurality of columns, such that service loop (376) may connect with both sensor (378) and cable (312). As will be described in greater detail below, service loop (376) is sufficiently long and loose such that sensor assembly (360) may rotate relative to casing (316) without disrupting the connection between service loop (376) and both sensor (378) and cable (312).

Communication assembly (310) includes casing (316), cable (312) attached to casing (316) via a cable mount (315), and a USB plug (311) attached to the opposite end of cable (312). Cable mount (315) attaches cable (312) with casing (316). Cable (312), USB plug (311), and service loop (376) are configured to provide a conduit for communication between sensor (378) and processor (110) during exemplary use. Therefore, USB plug (311) may directly connect with console (116) such that sensor (378) is in wired communication with processor (110) via cable (312) and service loop (376). Alternatively, service loop (376), cable (312), USB plug (311) may connect sensor (378) with a wireless communication device that is in wireless communication with console (116), similar to how coupling unit (132) establishes wireless communication between navigation guidewire (130) and console (116). Cable (312), service loop (376), and USB plug (311) may provide a conduit for communication between sensor (378) and processor (110) through any suitable techniques known to one having ordinary skill in the art in view of the teachings herein.

Figure 11:
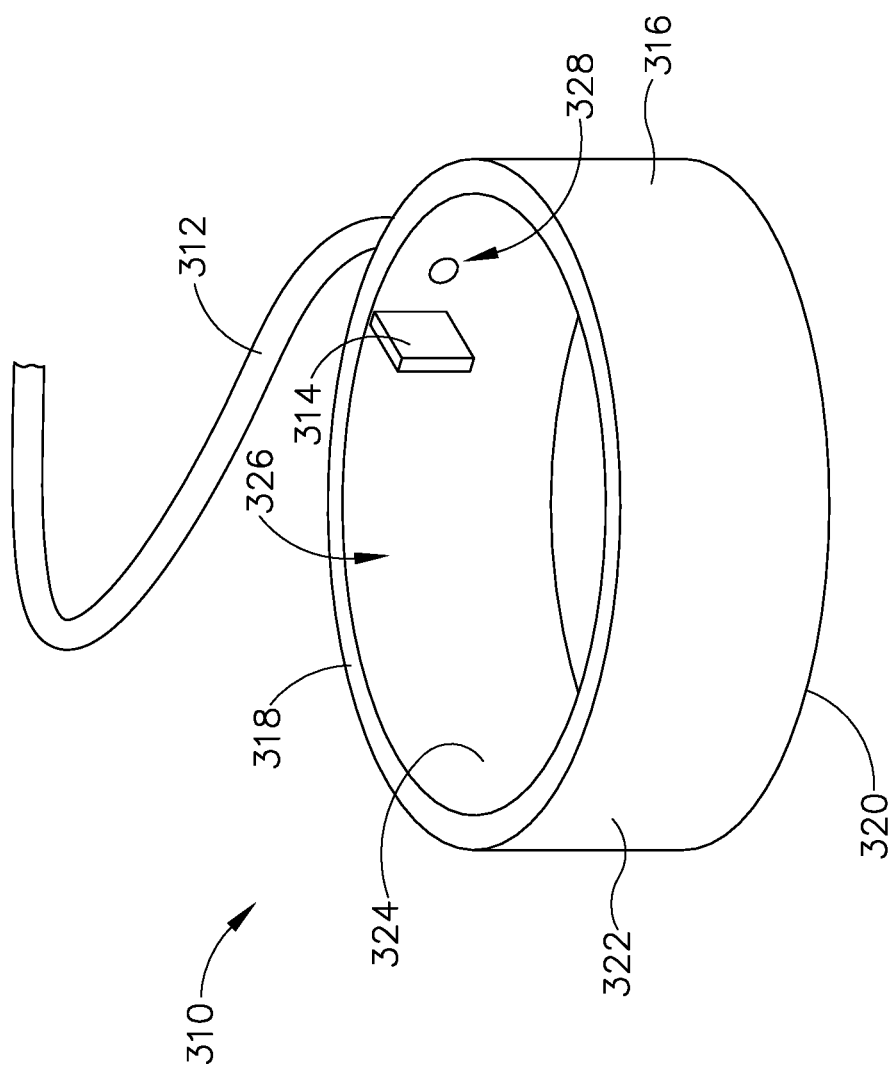
FIG. 11 depicts a perspective view of a communication assembly of the patient tracking device of FIG. 7.

As best seen in FIG. 11, casing (316) includes a top surface (318), a bottom surface (320), an exterior surface (322), interior surface (324), and second rotation stop (314) extending radially inwardly from interior surface (324). As mentioned above, second rotation stop (314) is dimensioned to abut against first rotation stop (364) to limit rotation of communication assembly (310) relative to sensor assembly (360). Casing (316) defines a cavity (326) to rotationally house sensor assembly (360). Casing (316) also defines a coupling channel (328) extending from interior surface (324) to exterior surface (322). Coupling channel (328) is located adjacent to cable (312) to provide a pathway for service loop (376) to couple with cable (312).

Top surface (318) abuts against interior surface (368) of cap (362) when sensor assembly (360) and communication assembly (310) are assembled. Similarly, bottom surface (320) abuts against interior surface (374) of base (370) when sensor assembly (360) and communication assembly (310) are assembled. Top surface (318) and bottom surface (320) of casing (316) abut against interior surfaces (368, 374) of cap (362) and base (370), respectively, when assembled to prevent sensor assembly (360) from disassociating with casing (316).

Figure 12A:
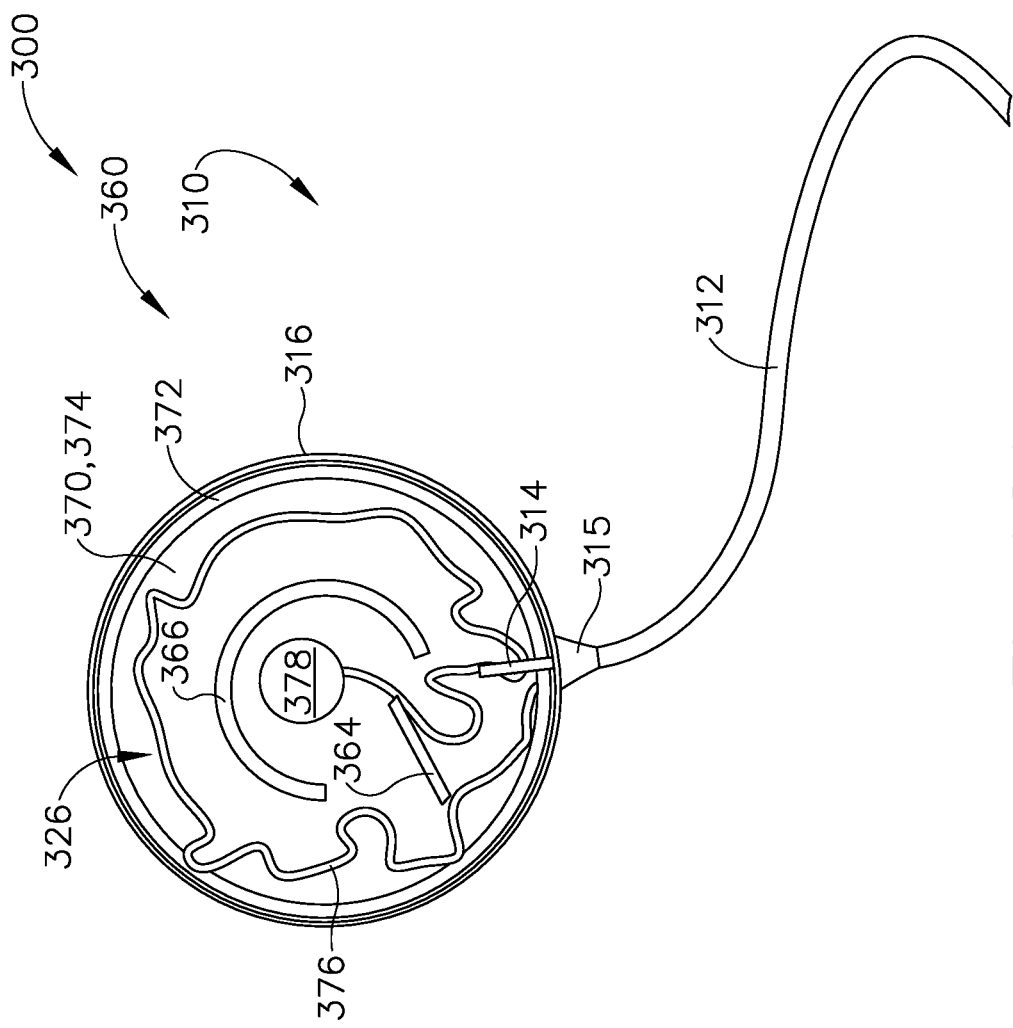
FIG. 12A depicts a cross-sectional view of the patient tracking device of FIG. 7, taken along line 12-12 of FIG. 7, where the sensor assembly of FIG. 9 is in a first rotational position relative to the communication assembly of FIG. 11.
Figure 12B:
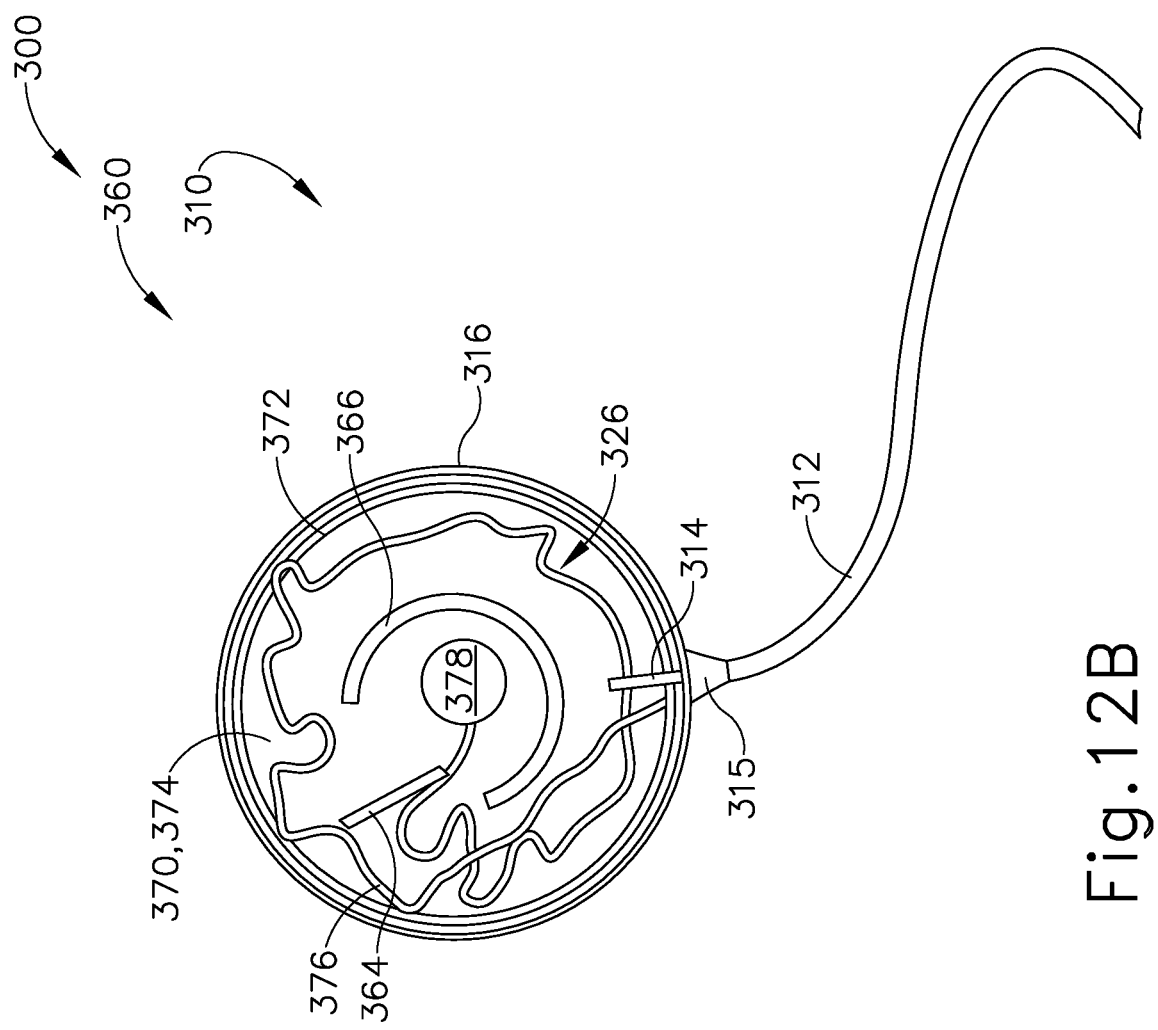
FIG. 12B depicts a cross-sectional view of the patient tracking device of FIG. 7, taken along line 12-12 of FIG. 7, where the sensor assembly of FIG. 9 is in a second rotational position relative to the communication assembly of FIG. 11.

During exemplary use, an operator may attach patient tracking assembly (300) to the head (H) of a patient (P) via the adhesive material on exterior surface (371) of base (370), thereby fixing sensor assembly (360) to the patient (P). As shown in FIGS. 12A-12B, if an operator determines that cable (312) is an obstruction, the operator may rotate communication assembly (310) relative to sensor assembly (360) without affecting the position of sensor (378) relative to patient (P). It should be understood that FIGS. 12A-12B show movement from the perspective of communication assembly (310) rather than sensor assembly (360). Service loop (376) is sufficiently long and loose such that as casing (316) rotates relative to sensor (378), the connection between cable (312) and sensor (378) provided by service loop (376) is not disrupted or damaged. Therefore, the operator may move cable (312) out of the way so that cable (312) is no longer an obstruction without affecting the accuracy of sensor (378) during exemplary operation.

It should be understood that if casing (316) rotates too far relative to sensor assembly (360), rotation stops (314, 364) will abut against each other, thereby helping prevent potential overextension of service loop (376). However, rotation stops (314, 364) are entirely optional. While in the current example, service loop (376) is used to establish an uninterrupted connection between cable (312) and sensor (378) while simultaneously allowing cable (312) to rotate relative to sensor (378), any other suitable connection may be used as would be apparent to one having ordinary skill in the art in view of the teachings herein. For example, a slip ring assembly may be incorporated into suitable portions of communication assembly (310) and sensor assembly (360), thereby providing full electrical continuity between the two assemblies while also allowing relative rotation. Sensor (378) and cable (312) may be in communication with respective slip rings through any suitable connection as would be apparent to one having ordinary skill in the art in view of the teachings herein, such as electrical traces embedded into base (370) and casing (316), respectively.

With cable (312) in the desired orientation relative to patient (P), an operator may then communicatively couple USB plug (311) with processor (110) in accordance with the description above. During exemplary use, sensor (378) may be responsive to movement within fields generated by field generators (506). Signals generated by movement of sensor (378) may be sent to processor (110). Because sensor (378) is fixed to head (H) of patient (P) in accordance with the description above, signals generated by movement of sensor (378) may be indicative of movement of head (H). If a patient (P) does move head (H) during an exemplary procedure, cable (252) may be prevented from bending or pulling relative to sensor assembly (360) since casing (312) and cable (312) may rotate relative to sensor assembly (360).

Additionally, signals generated by movement of sensor (378) may allow processor (110) to determine the three-dimensional location of head (H) of patient (P) relative to the plurality of field generators (506) fixed to support assembly (500). Processor (110) may utilize this information, in conjunction with the location of navigation guidewire (130) (or any other suitable instrument) relative to field generators (506), such that processor (110) and display screen (114) may properly display the location of navigation guidewire (130) (or any other suitable instrument) within head (H) of patient (P).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a processing assembly; (b) a plurality of field generator elements in communication with the processing assembly, wherein the plurality of field generator elements are configured to generate an electromagnetic field; and (c) a patient tracking assembly in communication with the processing assembly, wherein the patient tracking assembly comprises: (i) a sensor assembly, wherein the sensor assembly comprises: (A) a first body configured to selectively attach to a patient, (B) a first sensor mounted to the first body, wherein the first sensor is configured to generate a signal in response to movement within the electromagnetic field, and (C) an electrical conduit in electrical communication with the sensor, and (ii) a communication assembly, wherein the communication assembly comprises: (A) a second body coupled with the first body, wherein the second body is configured to rotate relative to the first body from a first rotational position to a second rotational position, and (B) a cable extending away from the second body, wherein the cable is configured to communicate with the processing assembly, wherein the cable is coupled with the electrical conduit, wherein the electrical conduit is configured to couple the first sensor with the cable while the casing is in the first rotational position and the second rotational position.

Example 2

The apparatus of Example 1, further comprising an instrument, wherein the instrument further comprises a second sensor, wherein the processing assembly is configured to process signals from the first sensor and the second sensor to determine the location of the instrument relative to an anatomical structure associated with the first sensor.

Example 3

The apparatus of any one or more of Examples 1 through 2, wherein the second body comprises a first rotational stop, wherein the sensor assembly comprises a second rotational stop, wherein the first rotational stop and the second rotational stop are configured to abut each other at a third rotational position.

Example 4

The apparatus of any one or more of Examples 1 through 3, wherein the first body of the sensor assembly comprises an adhesive material configured to selectively attach to the patient.

Example 5

The apparatus of any one or more of Examples 1 through 4, wherein the first body of the sensor assembly comprises a circumferential lip rotatably housed within the second body of the communication assembly.

Example 6

The apparatus of any one or more of Examples 1 through 5, further comprising a frame member, wherein the plurality of field generating elements are attached to the frame member.

Example 7

The apparatus of Example 6, further comprising a medical chair, wherein the frame is configured to attach to the medical chair.

Example 8

The apparatus of any one or more of Examples 1 through 7, wherein the sensor assembly further comprises a cap.

Example 9

The apparatus of Example 8, wherein the sensor assembly further comprises a connecting arm connecting the first body and the cap.

Example 10

The apparatus of Example 9, wherein the connecting arm comprises a semi-cylindrical shell.

Example 11

The apparatus of Example 10, wherein the first sensor is located within the semi-cylindrical shell.

Example 12

The apparatus of any one or more of Examples 1 through 11, wherein the electrical conduit comprises a service loop that extends from first sensor to the cable.

Example 13

The apparatus of Example 12, wherein the second body defines a coupling channel, wherein the service loop extends through the coupling channel to couple with the cable.

Example 14

The apparatus of Example 13, wherein the service loop is fixed to the first sensor at a first end and fixed to the cable at a second end.

Example 15

The apparatus of Example 14, wherein a portion of the service loop between the first end and the second end is free to move relative to the first body.

Example 16

An apparatus comprising: (a) a processing assembly; (b) a plurality of field generator elements in communication with the processing assembly, wherein the plurality of field generator elements are configured to generate an electromagnetic field; and (c) a patient tracking assembly in communication with the processing assembly, wherein the patient tracking assembly comprises: (i) a reusable portion comprising a coupling body, a sensor, and a cable, wherein the coupling body is attached to one end of the communication cable, wherein the sensor is configured to generate a signal in response to movement within the electromagnetic field, wherein the sensor is in communication with the cable, wherein the cable is configured to establish communication between the processing assembly and the sensor, and (ii) a disposable portion configured to attach to a patient, wherein the disposable portion comprises an attachment feature configured to selectively couple with the coupling body of the reusable portion.

Example 17

The apparatus of Example 16, wherein the disposable portion comprises a flexible adhesive pad, wherein the attachment feature is fixed to the flexible adhesive pad.

Example 18

The apparatus of any one or more of Examples 16 through 17, wherein the attachment feature defines a housing, wherein the housing is dimensioned to receive the coupling body.

Example 19

The apparatus of any one or more of Examples 16 through 18, wherein the sensor is fixed to the coupling body.

Example 20

An apparatus comprising: (a) a processing assembly; (b) a plurality of field generator elements in communication with the processing assembly, wherein the plurality of field generator elements are configured to generate an electromagnetic field; and (c) a patient tracking assembly in communication with the processing assembly, wherein the patient tracking assembly comprises: (i) a sensor configured to generate a signal when moved within the electromagnetic field, (ii) a coupling device configured to establish communication between the sensor and the processing assembly, and (iii) an attachment member configured to selectively attach to a patient, wherein the sensor is fixed to the attachment member, wherein the coupling device is configured to rotate relative to the attachment member.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a data processor;
   (b) a plurality of energy field generators in communication with the data processor, wherein the plurality of energy field generators are configured to generate an electromagnetic field; and
   (c) a patient tracking assembly in communication with the data processor, wherein the patient tracking assembly comprises:
      (i) a sensor assembly, wherein the sensor assembly comprises:
         (A) a first body configured to selectively attach to a patient,
         (B) a first sensor mounted to the first body, wherein the first sensor is configured to generate a signal in response to movement within the electromagnetic field, and
         (C) an electrical conduit in electrical communication with the first sensor, and
      (ii) a communication assembly, wherein the communication assembly comprises:
         (A) a second body coupled with the first body, wherein the second body is configured to rotate relative to the first body and relative to the first sensor from a first rotational position to a second rotational position, and
         (B) a cable coupled with a surface of the second body, wherein the cable is configured to communicate with the data processor, wherein the cable is coupled with the electrical conduit, wherein the electrical conduit is configured to couple the first sensor with the cable while the second body is in the first rotational position and the second rotational position.

2. The apparatus of claim 1, further comprising an instrument, wherein the instrument further comprises a second sensor, wherein the data processor is configured to process signals from the first sensor and the second sensor to determine a location of the instrument relative to an anatomical structure.

3. The apparatus of claim 1, wherein the second body comprises a first rotational stop, wherein the sensor assembly comprises a second rotational stop, wherein the first rotational stop and the second rotational stop are configured to abut each other at a third rotational position.

4. The apparatus of claim 1, wherein the first body of the sensor assembly comprises an adhesive material configured to selectively attach to the patient.

5. The apparatus of claim 1, wherein the first body of the sensor assembly comprises a circumferential lip rotatably housed within the second body of the communication assembly.

6. The apparatus of claim 1, further comprising a frame member, wherein the plurality of energy field generators are attached to the frame member.

7. The apparatus of claim 6, further comprising a medical chair, wherein the frame is configured to attach to the medical chair.

8. The apparatus of claim 1, wherein the sensor assembly further comprises a cap.

9. The apparatus of claim 8, wherein the sensor assembly further comprises a connecting arm connecting the first body and the cap.

10. The apparatus of claim 9, wherein the connecting arm comprises a semi-cylindrical shell.

11. The apparatus of claim 10, wherein the first sensor is located within the semi-cylindrical shell.

12. The apparatus of claim 1, wherein the electrical conduit comprises a service loop that extends from the first sensor to the cable.

13. The apparatus of claim 12, wherein the second body defines a coupling channel, wherein the service loop extends through the coupling channel to couple with the cable.

14. The apparatus of claim 13, wherein the service loop is fixed to the first sensor at a first end and fixed to the cable at a second end.

15. The apparatus of claim 14, wherein a portion of the service loop between the first end and the second end is free to move relative to the first body.

16. An apparatus comprising:
   (a) a data processor;
   (b) a plurality of energy field generators in communication with the data processor, wherein the plurality of energy field generators are configured to generate an electromagnetic field; and
   (c) a patient tracking assembly in communication with the data processor, wherein the patient tracking assembly comprises:
      (i) a sensor assembly, wherein the sensor assembly comprises:
         (A) a first body having a surface configured to selectively attach to a patient,
         (B) a sensor mounted to the first body, wherein the sensor is configured to generate a signal in response to movement within the electromagnetic field, and
         (C) an electrical conduit in electrical communication with the sensor, and
      (ii) a communication assembly, wherein the communication assembly comprises:
         (A) a second body coupled with the first body, and
         (B) a cable coupled with the second body, wherein the cable is configured to communicate signals from the sensor to the data processor while the second body is in a first rotational position and a second rotational position, wherein the second body and the cable are each configured to rotate relative to the first body and relative to the sensor from the first rotational position to the second rotational position.

17. The apparatus of claim 16, wherein the electrical conduit is housed within a cavity formed between the first body coupled with the second body.

18. The apparatus of claim 16, wherein the electrical conduit comprises a service loop that extends from the sensor to the cable.

19. The apparatus of claim 18, wherein the second body includes a coupling channel, wherein the service loop extends through the coupling channel to couple with the cable.

20. An apparatus comprising:
 (a) a data processor;
 (b) a plurality of energy field generators in communication with the data processor, wherein the plurality of energy field generators are configured to generate an electromagnetic field; and
 (c) a patient tracking assembly in communication with the data processor wherein the patient tracking assembly comprises:
  (i) a sensor assembly, wherein the sensor assembly comprises:
   (A) a first body configured to selectively attach to a patient,
   (B) a sensor mounted to the first body, wherein the sensor is configured to generate a signal in response to movement within the electromagnetic field, and
   (C) an electrical conduit in electrical communication with the sensor, and
  (ii) a communication assembly, wherein the communication assembly comprises:
   (A) a second body coupled with the first body, wherein the second body is configured to rotate relative to the first body and relative to the sensor from a first rotational position to a second rotational position, wherein a surface of the second body includes a coupling channel; and
   (B) a cable coupled with the electrical conduit through the coupling channel, wherein the cable is configured to communicate signals from the sensor to the data processor.

\* \* \* \* \*